(12) United States Patent
Rabhi et al.

(10) Patent No.: US 9,999,647 B2
(45) Date of Patent: Jun. 19, 2018

(54) METHOD FOR OBTAINING A PLANT EXTRACT AND ASSOCIATED COMPOSITIONS

(71) Applicants: Ethnodyne, Paris (FR); Centre National de la Recherche Scientifique (CNRS), Paris (FR)

(72) Inventors: Chérif Rabhi, Bretigny sur Orge (FR); Léon Cariel, Paris (FR); Jamal Ouanzzani, Massy (FR); Guillaume Arcile, Les Ulis (FR)

(73) Assignees: Ethnodyne, Paris (FR); Centre National De La Recherche Scientifique (CNRS), Paris (FR)

( * ) Notice: Subject to any disclaimer, the term of this patent is extended or adjusted under 35 U.S.C. 154(b) by 0 days. days.

(21) Appl. No.: 14/973,308

(22) Filed: Dec. 17, 2015

(65) Prior Publication Data
US 2016/0101142 A1   Apr. 14, 2016

Related U.S. Application Data

(63) Continuation-in-part of application No. PCT/EP2014/062311, filed on Jun. 13, 2014.

(51) Int. Cl.
| | | |
|---|---|---|
| *A61K 36/00* | (2006.01) | |
| *A61K 36/81* | (2006.01) | |
| *A61K 36/185* | (2006.01) | |
| *A61K 36/68* | (2006.01) | |
| *A23L 33/105* | (2016.01) | |
| *A23L 33/135* | (2016.01) | |

(52) U.S. Cl.
CPC ............ *A61K 36/81* (2013.01); *A23L 33/105* (2016.08); *A23L 33/135* (2016.08); *A61K 36/185* (2013.01); *A61K 36/68* (2013.01); *A23V 2002/00* (2013.01); *A61K 2236/19* (2013.01)

(58) Field of Classification Search
USPC ......................................................... 424/725
See application file for complete search history.

(56) References Cited

U.S. PATENT DOCUMENTS

2010/0015109 A1* 1/2010 Bias ..................... A61K 35/744
424/93.44

* cited by examiner

*Primary Examiner* — Michael V Meller
(74) *Attorney, Agent, or Firm* — Christensen O'Connor Johnson Kindness PLLC

(57) ABSTRACT

The invention relates to a method for obtaining a composition from a plant extract, to assist in the treatment or prevention of disorders or diseases related to neovascularisation.

7 Claims, 26 Drawing Sheets

FIG. 15A | FIG. 15B
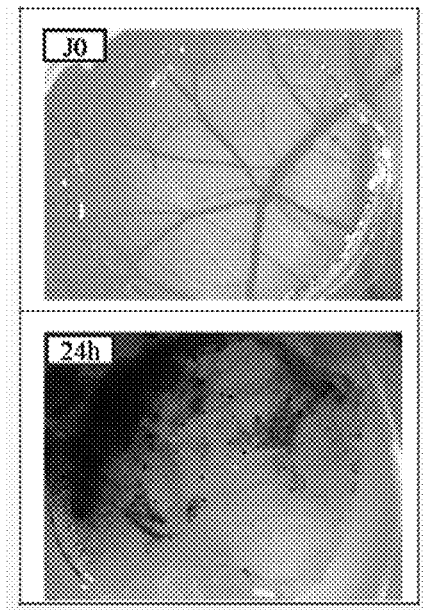 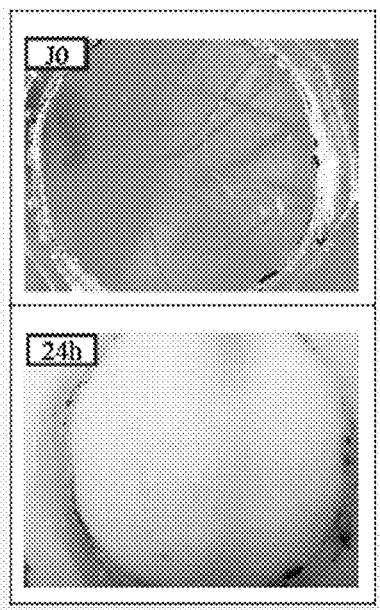
FIG. 15C | FIG. 15D
FIG. 16A | FIG. 16B
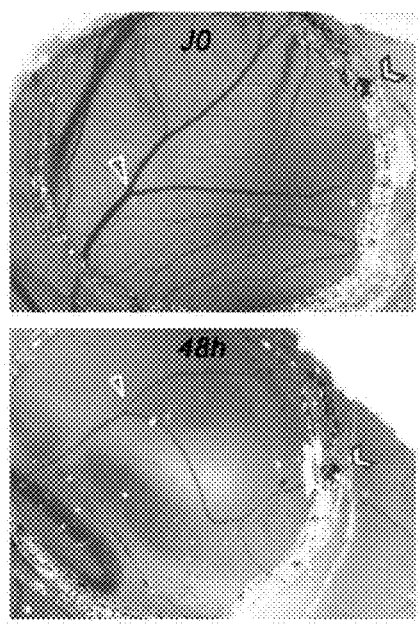 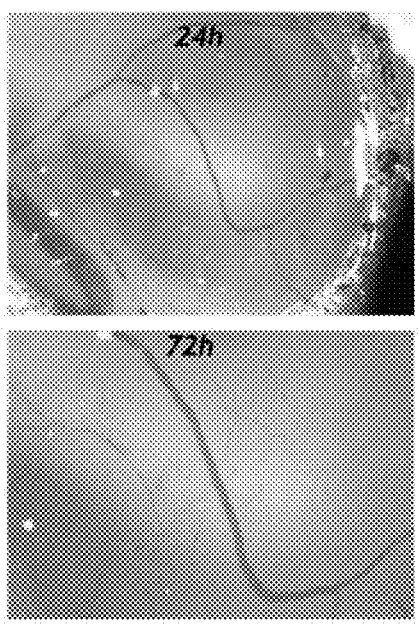
FIG. 16C | FIG. 16D

METHOD FOR OBTAINING A PLANT EXTRACT AND ASSOCIATED COMPOSITIONS

CROSS-REFERENCE TO RELATED APPLICATIONS

This application is a continuation-in-part of PCT/EP2014/062311, filed Jun. 13, 2014, which claims priority to French Application No. 1355652, filed Jun. 17, 2013, the disclosures of which are hereby incorporated by reference in their entirety.

STATEMENT REGARDING SEQUENCE LISTING

The sequence listing associated with this application is provided in text format in lieu of a paper copy and is hereby incorporated by reference into the specification. The name of the text file containing the sequence listing is 55072_Seq_Final_2015-12-15.txt. The text file is 3 KB; was created on Dec. 15, 2015; and is being submitted via EFS-Web with the filing of the specification.

BACKGROUND

The invention relates to a method for obtaining a composition from a plant extract, to assist in the treatment or prevention of disorders or diseases related to neovascularisation.

Angiogenesis or vascularisation is a highly regulated physiological phenomenon by which new blood vessels are produced in a tissue or an organ. The so-called "normal" angiogenesis is activated in wound healing situations or in the development of the foetal environment.

Pathological angiogenesis is activated by cellular or metabolic disorders, which may or may not be related to age, and is responsible for potentially highly disabling diseases. These include several eye diseases, the best known of which are ARMD (Age-Related Macular Degeneration), diabetic retinopathy, and a series of punctate keratopathies and glaucomas associated with anarchic vascularisation.

Pathological angiogenesis is also suspected in rheumatoid arthritis, osteoarthritis, Crohn's disease, atherosclerosis and the various forms of birthmarks appearing in childhood or related to hereditary diseases.

Finally, angiogenesis is fundamental in the development of solid tumours and metastases. Tumours in which angiogenesis is important also include benign tumours such as acoustic neuroma, neurofibroma, trachoma and pyogenic granuloma. The prevention of angiogenesis may stop the growth of these tumours and the resultant damage.

A number of molecules are known to have an inhibitory effect on neo-angiogenesis, such as protamine, tetrahydrocortisol, fumagillin, ascorbic acid derivatives, animal glycoproteins and cell factors such as interferon. However, the lack of efficacy of these molecules, their toxicity or their difficult administration, in particular for protein factors, limit their usefulness. In addition, users are increasingly sensitive to the origin of products, as well as to their method of administration, favouring, in particular, products of natural origin.

It has been reported that extracts of *Withania somnifera*, *Emblica officinalis* and *Bacopa monnieri* show anti-angiogenic activity. However, the extracts of these plants are not used as anti-angiogenics because of the high toxicity related to the obtaining of the extracts and, in particular, the extract from *Withania somnifera*.

Surprisingly, the applicant has found that by combining an extraction step and a fermentation step using filamentous fungi in a method starting with the plant *Withania somnifera*, it is possible to affect the toxicity of the extracts.

The purpose of the invention is therefore to provide a method for obtaining a non-toxic composition based on extracts of *Withania somnifera*, having an inhibitory effect on neovascularisation, as well as the compositions thus obtained.

The present invention thus relates to a method for obtaining a composition, comprising at least the following steps:
Production of an extract of *Withania somnifera*.
Fermentation of said extract by its incubation with a filamentous fungus in a suitable environment.

The invention also relates to a composition which may be obtained by the method of the invention.

Another object of the invention is the use of this composition as a food supplement.

Another object of the invention is the use of this composition as a medicinal product.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

Other objects, features, aspects and advantages of the invention will appear more clearly on reading the description and examples that follow:

FIGS. 15A, 15B, 15C and 15D show photographs of chick embryo chorioallantoic membrane (CAM) at 0 and 24 hours respectively after exposure to 40 µl of the composition of example 8 at 10 mg/mL. The biomicroscopy and photography of the CAM have been made before treatment, and at 24, 48 and 72 h after administration of the composition;

FIGS. 16A, 16B, 16C and 16D show photographs of chick embryo chorioallantoic membrane (CAM) at 0, 24, 48 and 72 hours respectively after exposure to 40 µl of the composition of example 9 at 10 mg/mL. The biomicroscopy and photography of the CAM have been made before treatment, and at 24, 48 and 72 h after administration of the composition;

DETAILED DESCRIPTION

Figure 1A:
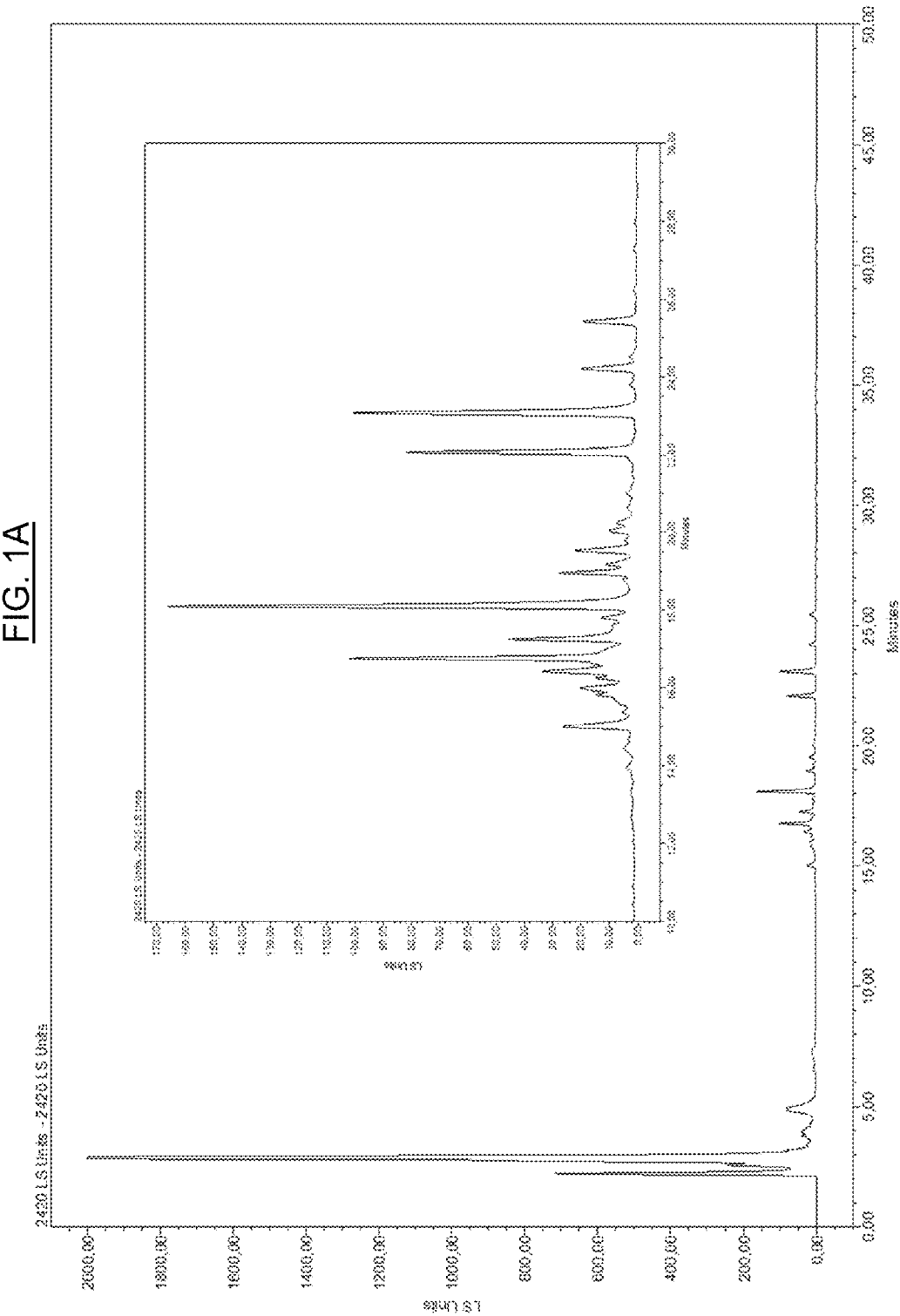
FIG. 1A shows a chromatographic fingerprint of the extract from the *Withania somnifera* extraction, without fermentation.

The *Withania somnifera* plant is obtained from India. The root of this plant is marketed by Alp Erbo (Marseille).

The extracts are produced using all the means known to a person skilled in the art, such as a maceration in aqueous, alcohol or alcohol-water solutions of plant powders derived from one or more of the various parts of the plant, such as the root, leaves, stem, branches, fruit or flowers, as well as by decoction, by supercritical or subcritical fluid extraction, and by adsorption. (Indian J Pharm Sci. 2010 September-October; 72(5): 659-663), EP2138054, thesis from the University of Toulouse, "Étude des procédés d'extraction et de purification de produits bioactifs à partir de plantes par couplage de techniques séparatives à basses et hautes pressions" [Study of the methods of extraction and purification of bioactive products from plants by coupling of separation techniques at low and high pressures] submitted by Petko Ivanov PENCHEV, 2010.

The filamentous fungus used for fermentation is selected from fungi of the family Cordycipitaceae. Preferably, the fungus is selected from among the fungi belonging to the genus *Beauveria*. Even more preferably, the filamentous fungus is derived from the strain *Beauveria bassiana*, more particularly the strain having reference ATCC 7159.

The strain *Beauveria bassiana* presents advantageous catalytic properties and is not toxic to humans. This strain is commonly used in agriculture in the biological fight against insects, as well as being used as a probiotic for animals.

Thus, the controlled fermentation, including that of the strain *Beauveria bassiana* ATCC 7159 (American Type Culture Collection), detoxifies the *Withania Somnifera* extract by a series of biocatalysis of various molecules contained in this extract and, more particularly, the chemical family of withanolide aglycones, the substances mainly responsible for the toxicity of the extract.

The term "fermentation" is used to mean the transforming of vegetable substances under the action of microorganisms.

The term "suitable medium" is used to mean any medium known to a person skilled in the art that is used to grow the fungal biomass required for the fermentation. Examples of suitable media are Sabouraud Dextrose Agar (SAB) (Gibco, France), Brain-Heart Infusion Agar (BHI) (Gibco, France), Malt Extra Broth (MEB) (Gibco, France), Yeast Malt extract (YM) (Gibco, France), Yeast Extract-Phosphate Medium (YEP) (Gibco, France), Dermatophyte Test Medium (DTM) (Gibco, France), Potato dextrose Agar and Broth (PDA, RDB) (Gibco, France), or C-Medium. Preferably, C-Medium having the following composition is used. 10 g of molasses, 0.5 g of $MgSO_4$, 2 g of $NaNO_3$, 0.5 g of KCl and 0.02 g of $FeSO_4$ added to 1 litre of water (compounds obtained from Sigma, France).

The term "detoxification" is used to mean elimination by the microorganism of potentially toxic molecules in the medium.

According to one feature, the method according to the invention includes a filtration step of the incubation medium used during the fermentation stage, in order to eliminate the microorganism used during fermentation. This filtration step may be carried out by decantation or mechanical filtration, using any means known to a person skilled in the art, such as filter paper or filters.

According to another feature, the method according to the invention may include a sterilisation step that can be carried out by any means known to a person skilled in the art, including the use of an autoclave, for example at 120° C. for 20 minutes, by ultrafiltration or by irradiation.

Preferably, after the fermentation, filtration and sterilisation steps, the incubation medium is then subjected to an ultrafiltration in order to obtain the solution which constitutes the plant extract ((Millipore, Applied Membranes), *Ultrafiltration of a strongly clogging food fluid: flow limit, critical flow and cleanability of a polymeric membrane*, Ndeye Wemsy Diagne, Murielle Rabiller-Baudry, IUT Rennes, University of Rennes I, UMR CNRS 6226).

In a preferred embodiment, the method of the invention may be implemented for plants other than *Withania somnifera*. In particular, extracts may also be produced from *Emblica officinalis*, originating in India and marketed by Infrag, Bengalore), *Bacopa monnieri* (India) marketed by Alp Erbo (Marseille), *Punica granatum* (China) (Shanghai Brightol International Co, Ltd (Shanghai), *Curcuma longa* (India) (Omnipharm, Chambery), *Piper longum* (Thailand) (Omnipharm, Chambery), or *Calendula officinalis* (China) (Shanghai Brightol International Co, Ltd (Shanghai), using the same procedure).

According to another mode of production, the method of the invention includes the step of adding an *Emblica officinalis* extract and a *Bacopa monnieri* extract to the *Withania somnifera* extract, before carrying out fermentation of said extracts with said filamentous fungus, in a suitable medium.

According to this mode of production, the method involves independent extraction steps for each plant extract used in the realisation of the said preparation. That is to say, the plant extracts are produced independently of one another.

Another object of the invention relates to the composition derived from the method of the invention.

This composition according to the invention thus contains an extract of *Withania somnifera*. It may also include at least one of the following extracts: extracts of *Emblica officinalis, Bacopa monnieri, Punica granatum, Curcuma longa, Piper longum,* or *Calendula officinalis.*

Advantageously, this composition includes, by weight, between 5 and 100 g/L of *Withania somnifera*, preferably 20 g/L. Preferentially, this composition also includes one of the following extracts, expressed by weight:

- between 5 and 100 g/L of *Emblica officinalis*, preferably 15 g/L,
- between 5 and 100 g/L of *Bacopa monnieri*, preferably 15 g/L,
- between 5 and 50 g/L of *Punica granatum*, preferably 10 g/L,
- between 5 and 250 g/L of *Curcuma longa*, preferably 20 g/L,
- between 20 and 50 mg/L of *Piper longum*, preferably 30 mg/L,
- between 5 and 50 g/L of *Calendula officinalis*, preferably 10 g/L, Preferably, the composition according to the invention comprises an extract of the plants *Withania somnifera, Emblica officinalis* and *Bacopa monnieri* which can be obtained by the method of the invention.

The composition may be in liquid, gel, emulsion, solid or injectable form.

The composition according to the invention is formulated for topical, ophthalmic, transdermal, oral, rectal or parenteral administration.

A person skilled in the art of pharmaceutical formulation will implement the various useful forms for administration of the products and/or supplements of the invention.

The composition according to the invention may additionally include suspensions, emulsions, syrups containing conventionally used inert diluents, and possibly other substances such as wetting agents, sweeteners, preservatives, thickeners, colourings or any other substance known to a person skilled in the art suitable for oral or ocular administration, in particular ((sodium sorbate (E201) (Sigma-Aldrich), anthocyanin (E163) (FBC Industries, USA), sodium metabisulphite (E223) (Sigma-Aldrich), alpha-tocopherol (E307) (FBC Industries, USA).

The composition according to the invention may also comprise solvents or other excipients such as water, propylene glycol, vegetable oils or other suitable organic solvents.

The term "excipient" is used to mean any compound which does not interfere with the effectiveness of the biological activity of the composition according to the invention, and which is not toxic to the host to which it is administered.

The composition according to the invention may also contain adjuvants, such as wetting agents, isotoning agents, emulsifiers, salts or any other substances known to a person skilled in the art that can be used as adjuvants (Polydimethylsiloxane, polyvinyl alcohol (PVA), hydrogels (Carbopol), polyvinylpyrrolidone, hydroxypropyl cellulose (HPC), poloxamer 188, EDTA, chlorobutanol) (Lubrizol, France, Dow Corning, USA).

Advantageously, the composition according to the invention may comprise other substances in the formulation of the said food supplement or drug, such as vitamins, mineral salts, a pharmaceutically acceptable vector, stabilisers, antioxidants, or any other substance known to a person skilled in the art and intended to be integrated into a food supplement or drug.

The terms "pharmaceutically acceptable vector" is used to mean any vector which does not interfere with the effectiveness of the biological activity of the composition according to the invention and which is not toxic to the host to which it is administered.

Following this process, the composition obtained is usable for a mammal, and more particularly for humans, to assist in the treatment or prevention of disorders or diseases linked to neovascularisation.

Said composition can thus be used as a food supplement.

The term "food supplement" is used to mean a product containing said composition and intended to supplement the food by providing nutrients that are beneficial to health according to the definition given by European directive 2002/46/EC. For example, a food supplement may be a capsule or a tablet for swallowing, or a powder or small vial to mix with a food and providing beneficial health effects.

Said composition can also be used as a medicinal product.

The term "medicinal product" is used to mean a product containing an accurate dose of said preparation according to European directive 65/65/EC, namely any substance or composition described as possessing curative or preventive properties with respect of human or animal disease. For example, the medicinal product containing said preparation at therapeutic doses can be administered orally as a capsule or a tablet, or injected intravitreously, or via any other route to confer the beneficial effects.

The composition according to the invention can be used to assist in the treatment or the prevention of disorders or diseases linked to neovascularisation, such as ARMD, diabetic retinopathy, punctate keratopathies and glaucomas associated with anarchic vascularisation. It is also useful in the treatment of rheumatoid arthritis, osteoarthritis, Crohn's disease, atherosclerosis, the various forms of birthmarks appearing in childhood or related to hereditary diseases, for the treatment of cancer and, more particularly, of solid tumours and metastases, as well as for the treatment of benign tumours such as acoustic neuroma, neurofibroma, trachoma and pyogenic granuloma.

The daily dose of the compositions and/or supplements according to the invention may vary according to the needs and severity of symptoms of the patient. Typically, the daily dose is between 10 mg/ml and 300 mg/ml of the solution after fermentation.

Preferably, the daily dose for an adult human is between 30 and 100 mg/ml of the solution after fermentation.

The present invention is now described using embodiments, which are for illustration purposes only and do not limit the scope of the invention.

EXAMPLE 1

Extract of *Withania somnifera* before Fermentation

The extract of *Withania somnifera* (originating in Southern Asia and sourced from India) was produced from a quantity of 650 g of root (Alp Erbo, Marseille), in a mixture of 8 litres of alcohol-water solvent, ethanol/water (60:40).

An amorphous extract of 87 g was obtained, i.e. a yield of 13.4%, which contained withanosides A and B, withanosides and sitoindosides (FIG. 1A).

In order to eliminate the withanolides considered to be toxic, a liquid/liquid extraction was carried out with $CH_2Cl_2$. After rinsing and drying the organic phase, 81.5 g of amorphous powder was obtained, i.e. a yield of 94%.

Figure 1B:
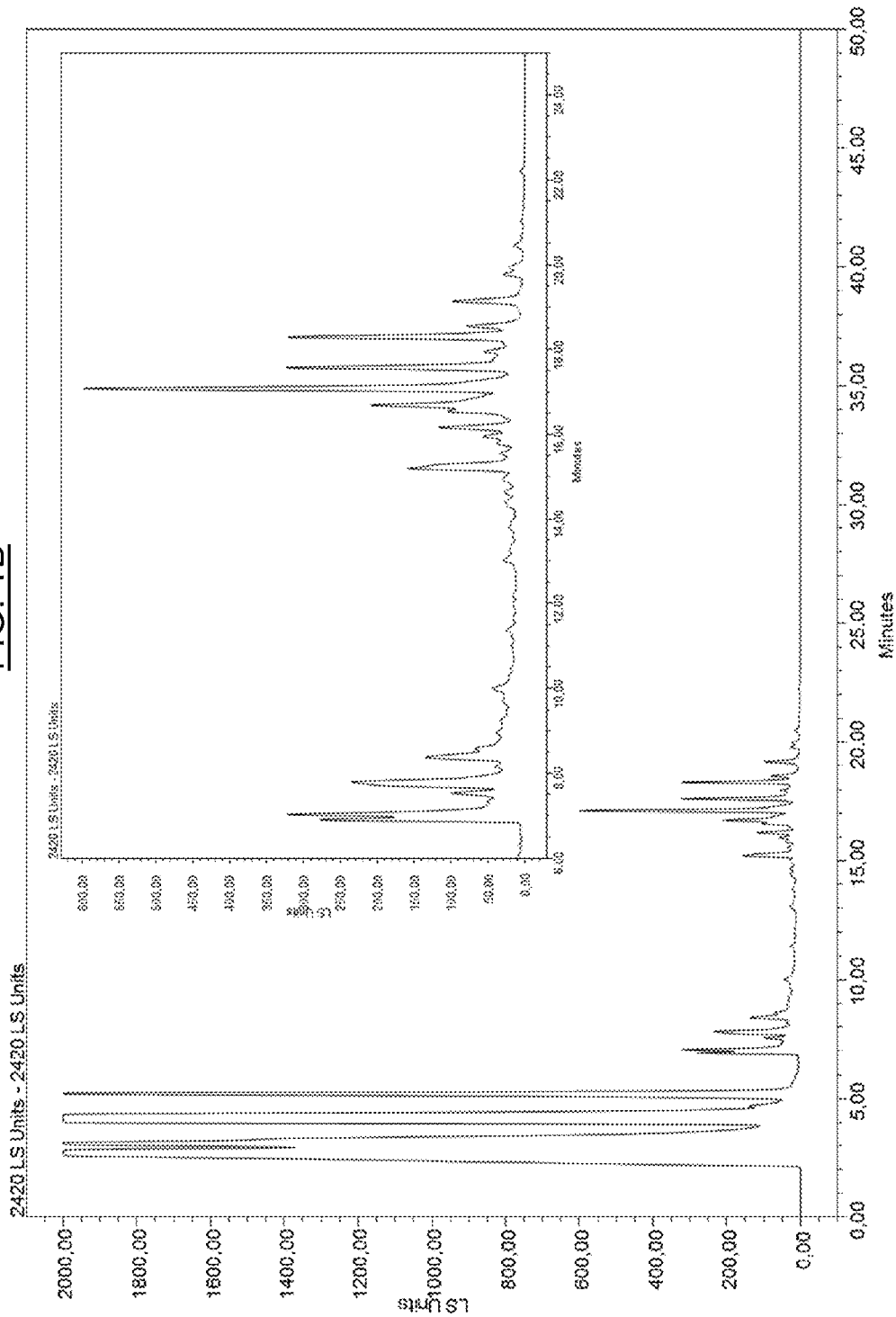
FIG. 1B shows a chromatographic fingerprint of the non-fermented extract from the *Withania somnifera* extraction, without withanolides.

This extract was subsequently analysed and then identified by HPLC, HPLC-MS and NMR techniques, in order to obtain a chromatographic fingerprint of the *Withania somnifera* extract (FIG. 1B).

The samples obtained were analysed on an HPLC system equipped with a Sunfire III C18 (4.6×150 mm) 3.5 μm (Waters) reversed-phase column, an Alliance® Waters W2695 HPLC system fitted with a Waters 2996 PDA detector. This chromatographic system was coupled to a Waters 2424 evaporative light scattering detector (ELSD). The HPLC system was controlled by the Empower 2 software (Waters).

The solvents used were composed of HPLC water (milli Q)+0.1% Formic Acid, acetonitrile (HPLC grade)+0.1% Formic Acid. The standard gradient used was 0 to 100% acetonitrile in 40 min+10 min to 100% acetonitrile (total duration 50 minutes). The flow rate was 0.7 ml/min and the injection volume 20 to 100 μl depending on the sample.

For the mass spectrometry, HPLC-MS analyses were carried out on a Waters Alliance® HPLC system coupled to a Waters 2998 PDA type UV detector, a Waters 2420 evaporative light scattering detector ELSD and a Micromass® ZQ mass detector (Waters).

The solvents were composed of HPLC water (milli Q)+0.1% Formic Acid and acetonitrile (HPLC grade)+0.1% Formic Acid. The standard gradient used was 0 to 100% acetonitrile in 40 min+10 min to 100% acetonitrile (total duration 50 minutes). The flow rate was 0.7 ml/min and the injection volume was 20 to 100 depending on the sample.

The samples of each composition for HPLC analysis were 0.45 micron filtered (Ait-France, ref: SFNY 013045N) and then a volume of the order of 50 μl was injected.

EXAMPLE 2

*Bacopa monnieri* Extract before Fermentation

The *Bacopa monnieri* extraction was carried out starting with a quantity of order of 418 g in a mixture of 5 litres of alcohol-water solvent, ethanol/water (50:50).

An amorphous extract of 77.1 g was obtained, i.e., a yield of 18.4%, which contains bacosides A and B.

Figure 2:
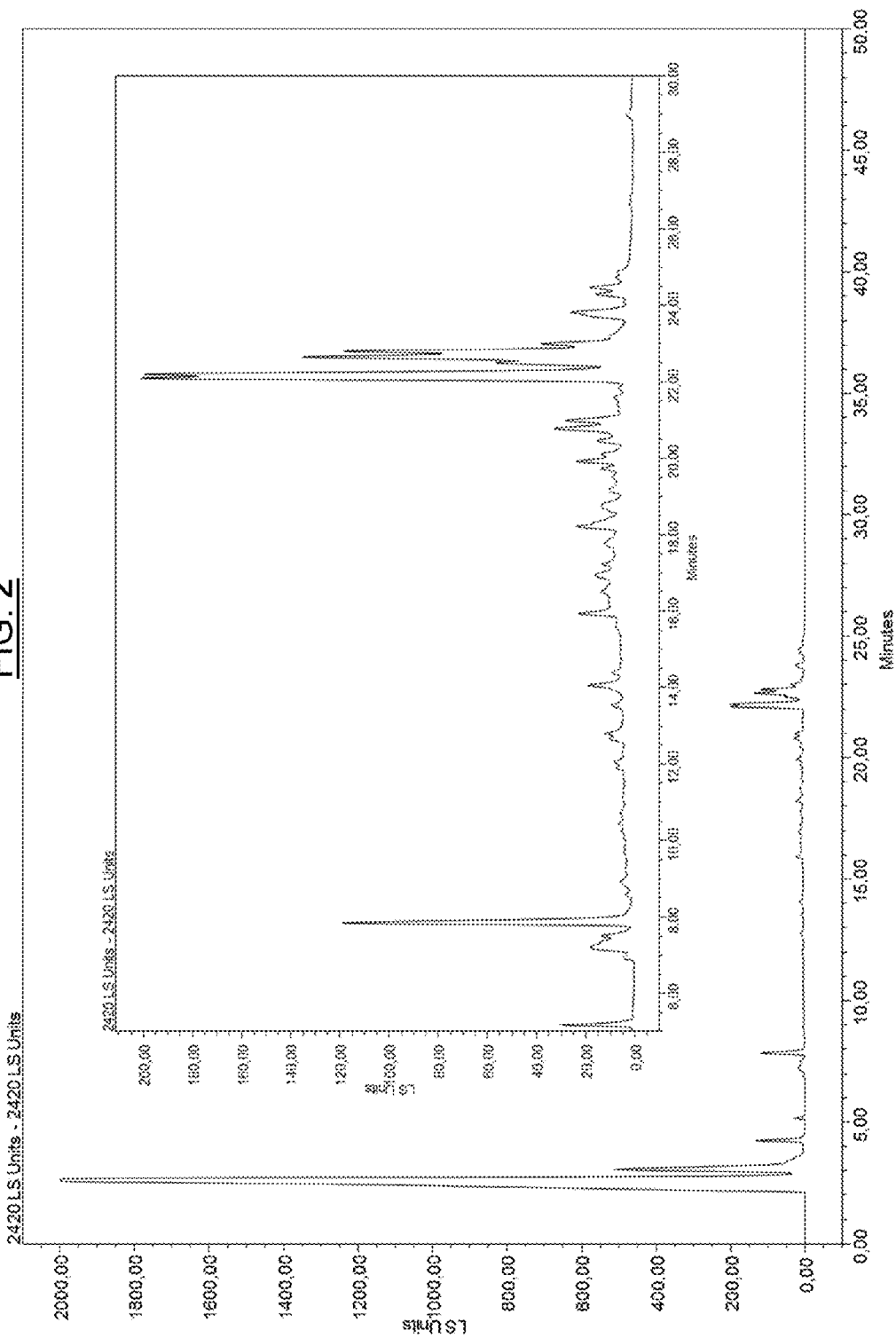
FIG. 2 shows a chromatographic fingerprint of the extract from the *Bacopa monnieri* extraction, without fermentation.

This extract was analysed and then identified by HPLC, HPLC-MS and NMR techniques, in order to obtain a chromatographic fingerprint of the *Bacopa monnieri* extract (FIG. 2).

EXAMPLE 3

Extract of *Emblica officinalis* before Fermentation

The *Emblica officinalis* extraction was carried out on a quantity of order of 512 g in a mixture of 7 litres of alcohol solvent comprising 100% ethanol.

An amorphous extract of 166.5 g was obtained, i.e., a yield of 32.5%, which contained gallic tannins, vitamin C and ellagic acid.

Figure 3:
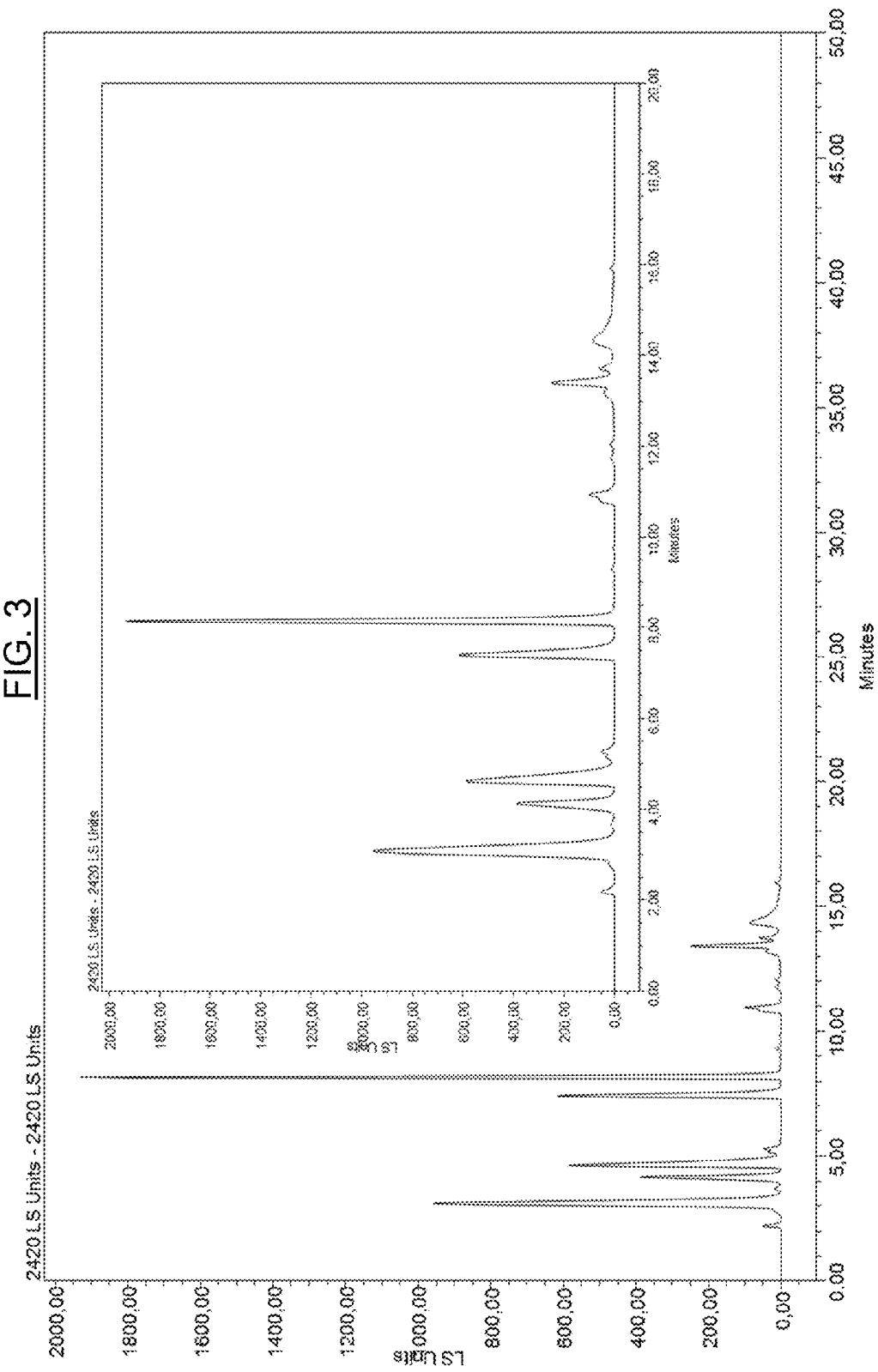
FIG. 3 shows a chromatographic fingerprint of the extract from the *Emblica officinalis* extraction, without fermentation.

This extract was analysed and then identified by HPLC, HPLC-MS and NMR techniques, in order to obtain a chromatographic fingerprint of the *Emblica officinalis* extract (FIG. 3).

EXAMPLE 4

Extract of *Calendula officinalis* before Fermentation

The *Calendula officinalis* extract, titrated with 10% lutein and 0.9% zeaxanthin, was obtained from Shanghai Brightol International Co, (Shanghai).

Figure 4:
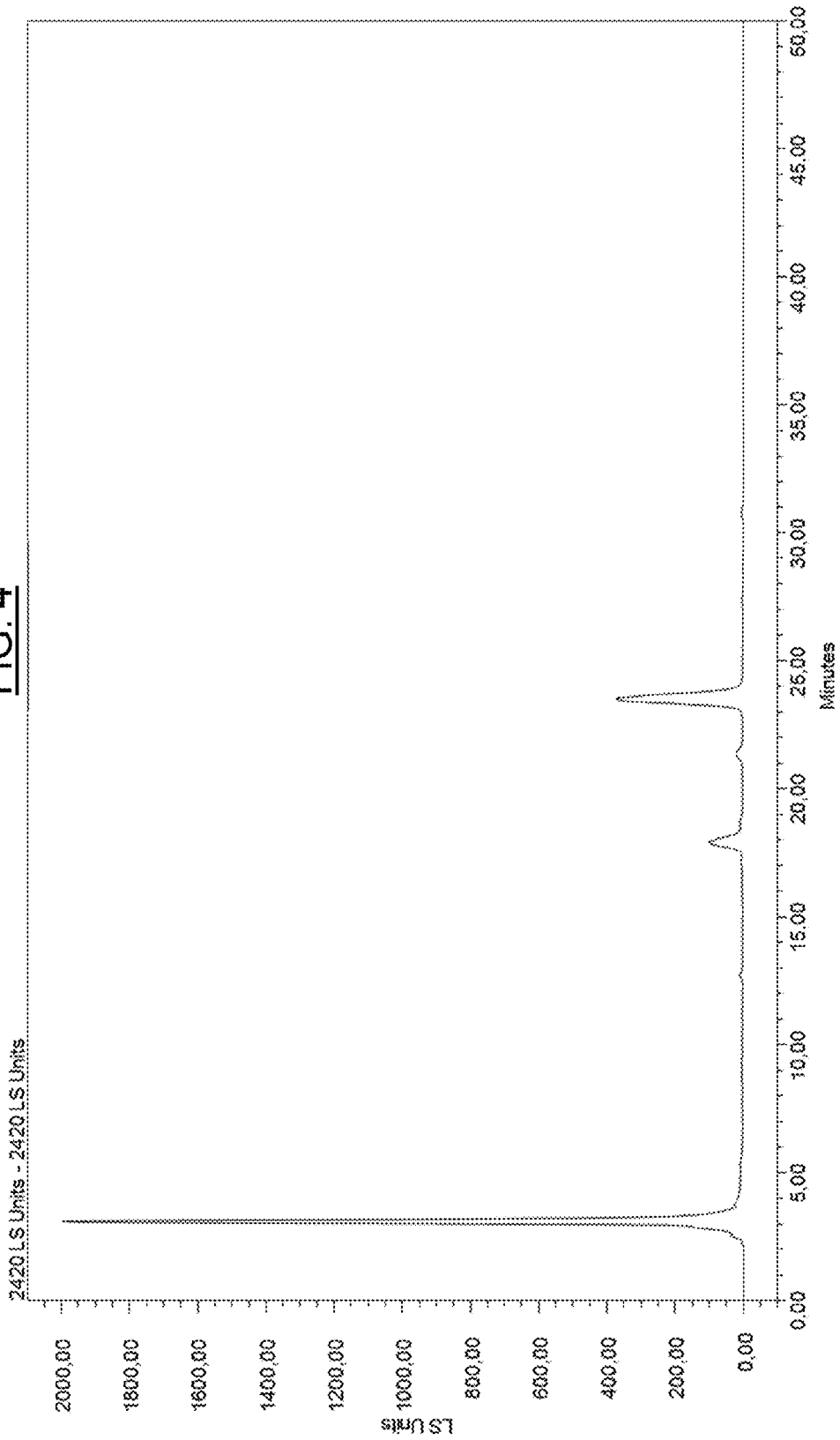
FIG. 4 shows a chromatographic fingerprint of the extract from the *Calendula officinalis* extraction, without fermentation.

This extract was analysed and then identified by HPLC, HPLC-MS and NMR techniques, in order to obtain a chromatographic fingerprint of the *Calendula officinalis* extract (FIG. 4).

EXAMPLE 5

Extract of *Punica granatum* before Fermentation

The *Punica granatum* extract, titrated with 40% ellagic acid was obtained from Shanghai Brightol International Co, Ltd (Shanghai).

Figure 5:
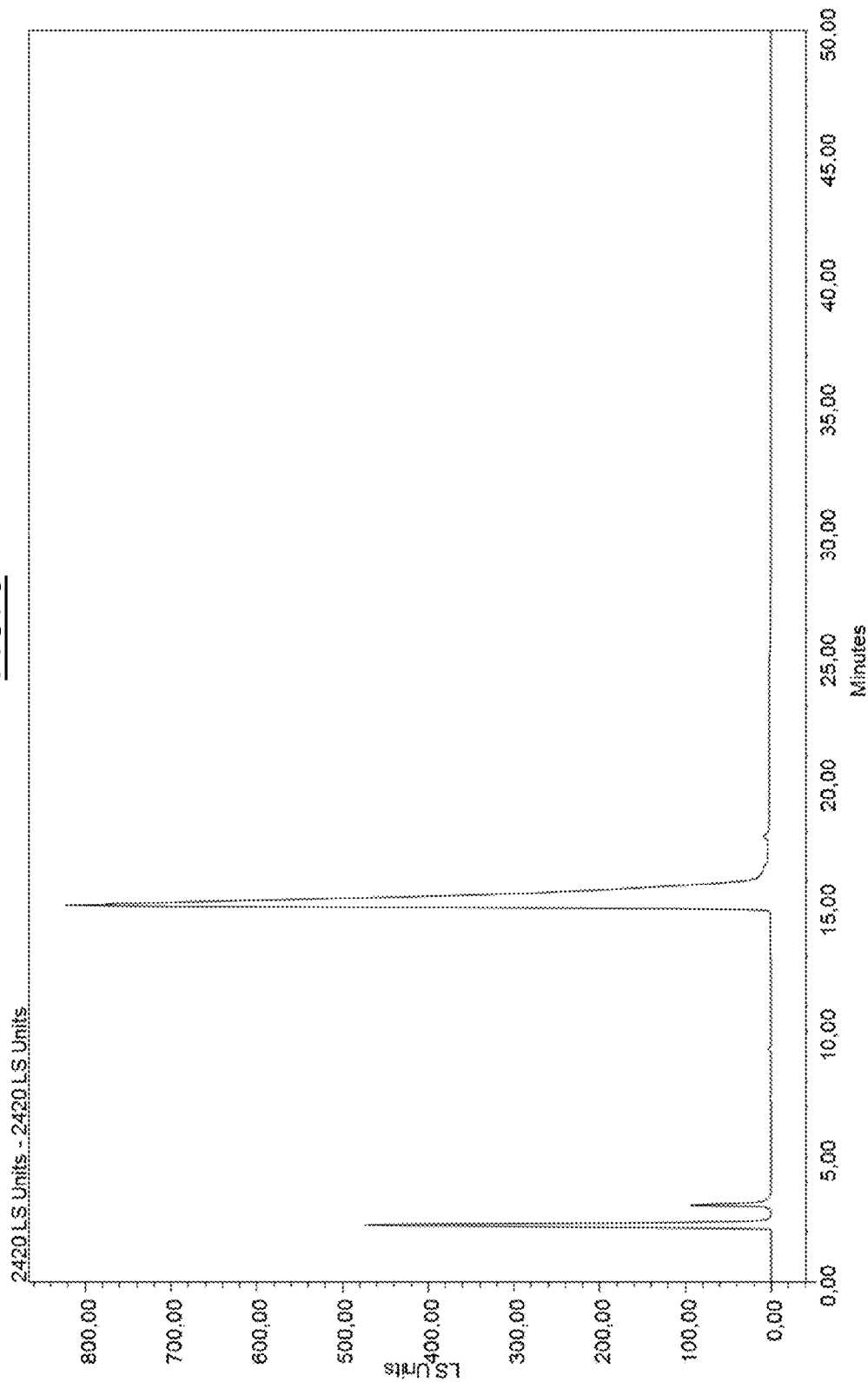
FIG. 5 shows a chromatographic fingerprint of a commercial extract of *Punica granatum*, without fermentation.

This extract was analysed and then identified by HPLC, HPLC-MS and NMR techniques, in order to obtain a chromatographic fingerprint of the *Punica granatum* extract (FIG. 5).

EXAMPLE 6

Extract of *Curcuma longa* before Fermentation

The extract of *curcuma* rhizome titrated with 95% curcumin came from COOPER, Melun, (Batch no.: 120 105 B, CE no. 207-280-5).

Figure 6:
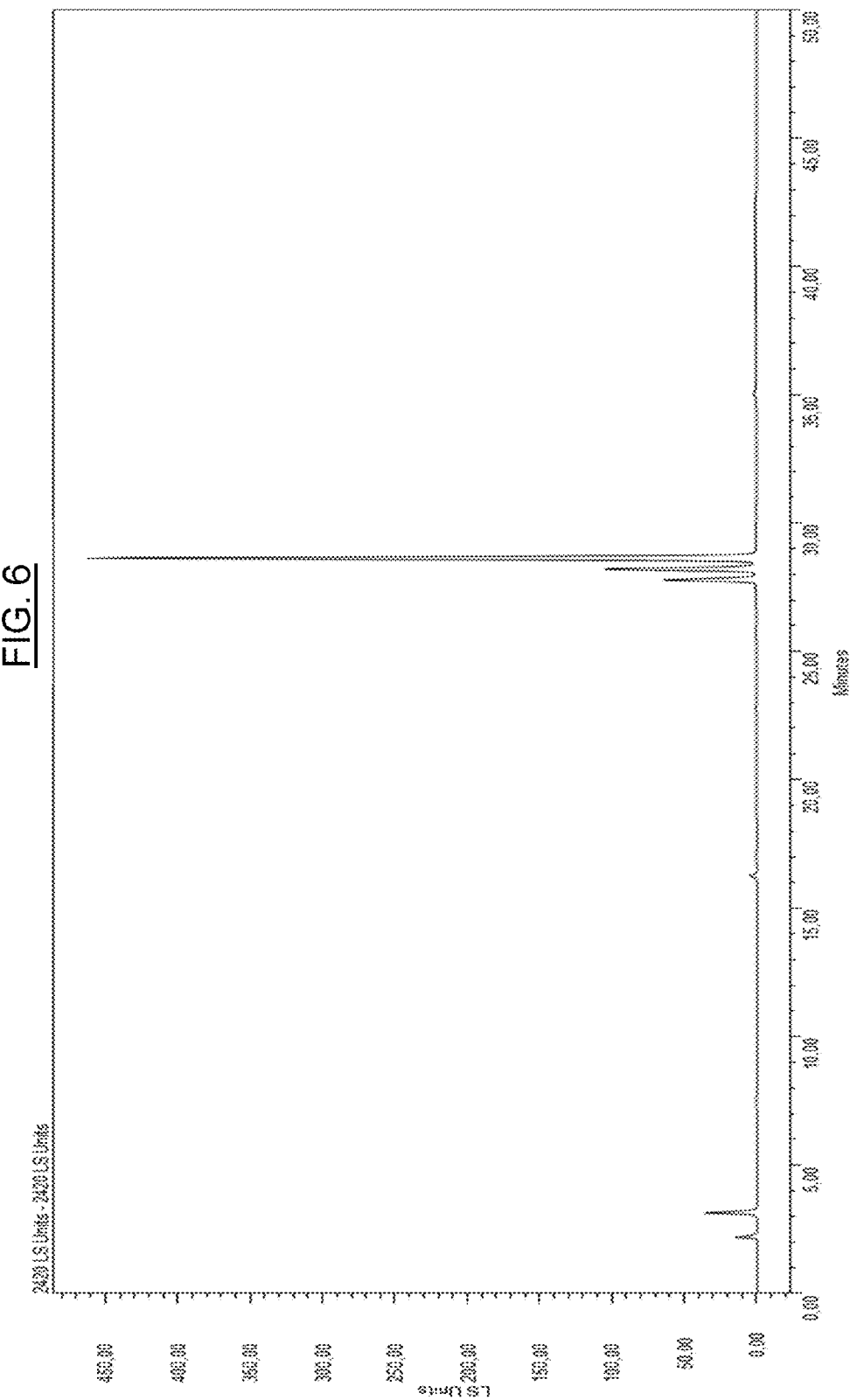
FIG. 6 shows a chromatographic fingerprint of a commercial extract of *Curcuma longa*, without fermentation.

This extract was analysed and then identified by HPLC, HPLC-MS and NMR techniques, in order to obtain a chromatographic fingerprint of the *Curcuma longa* extract (FIG. 6).

EXAMPLE 7

*Piper longum* Powder before Fermentation

The *Piper longum* was used as powder, which contains piperine.

Figure 7:
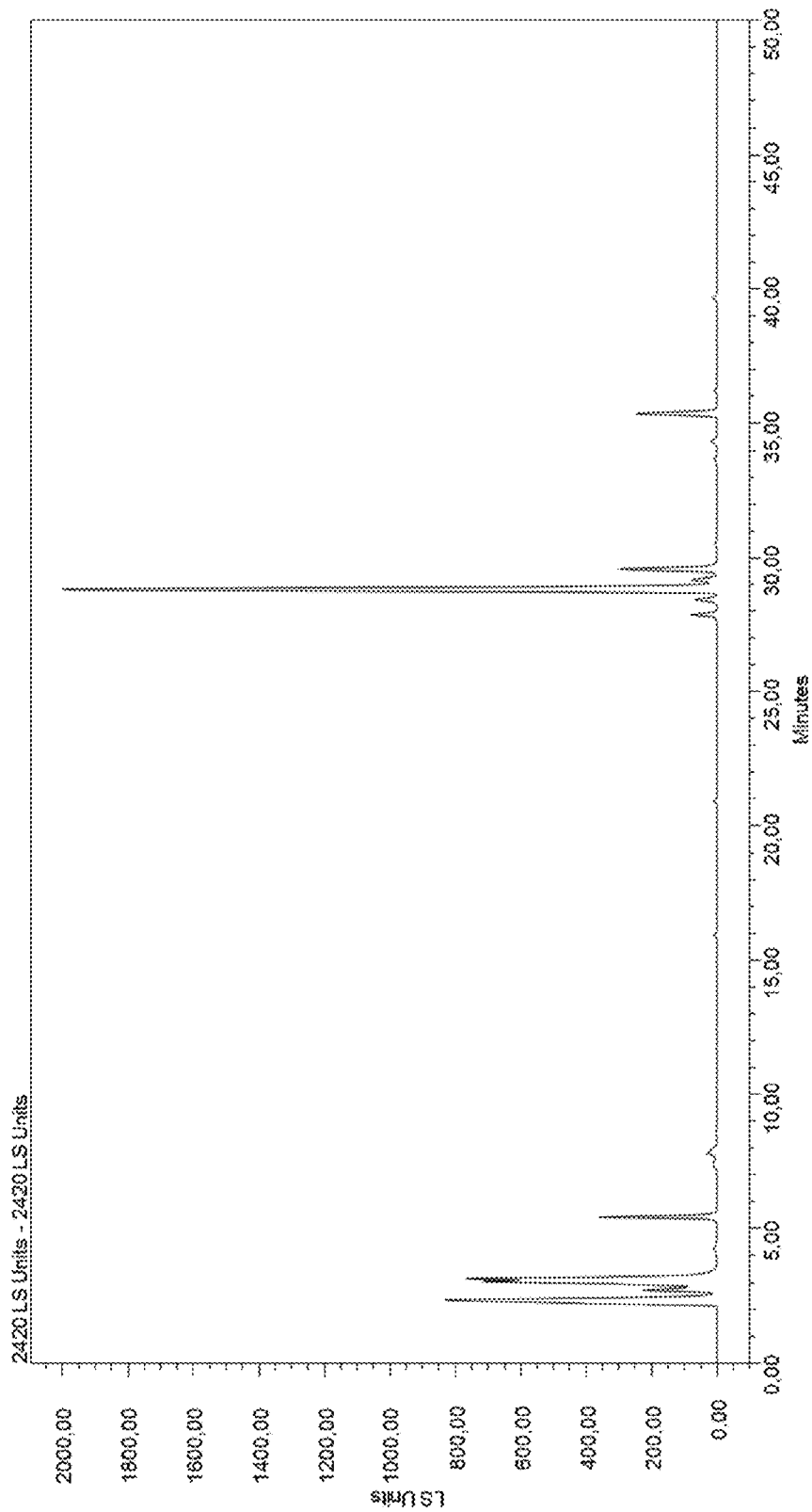
FIG. 7 shows a chromatographic fingerprint of the extract from the *Piper longum* extraction, without fermentation.

This powder was analysed and then identified by HPLC, HPLC-MS and NMR techniques, in order to obtain a chromatographic fingerprint of the *Piper longum* (FIG. 7).

EXAMPLE 8

Composition Containing Plant Extracts before Fermentation

A composition containing an extract of *Withania Somnifera* at a concentration of 20 g/L, of *Emblica officinalis* at a concentration of 15 g/L and of *Bacopa monnieri* at a concentration of 15 g/L was prepared from plants.

The plant material was briefly ground. Each plant was chopped independently of other plants, using grinders of the HGB50E-Blender type, so as to obtain the finest powders possible, of the order of 80 microns in diameter.

Extractions were then performed for each plant extract by maceration. During such extraction by maceration, the temperature is between 40° C. and 60° C. and the pressure is 100 bar during the two 1-hour cycles. After extraction, the heterogeneous solutions obtained were filtered on filter paper with a thickness of 870 μm and a diameter of 170 mm. The solutions obtained were collected and concentrated under reduced pressure using a BUCHI R-220-SE Rotavapor to provide an aqueous solution. These solutions were frozen at −80° C., before being deposited in a freeze dryer at −55° C. and under a pressure of 0.1 mbar (Edwards Modulyo Freeze Dryer) to produce the dried extracts.

Figure 8:
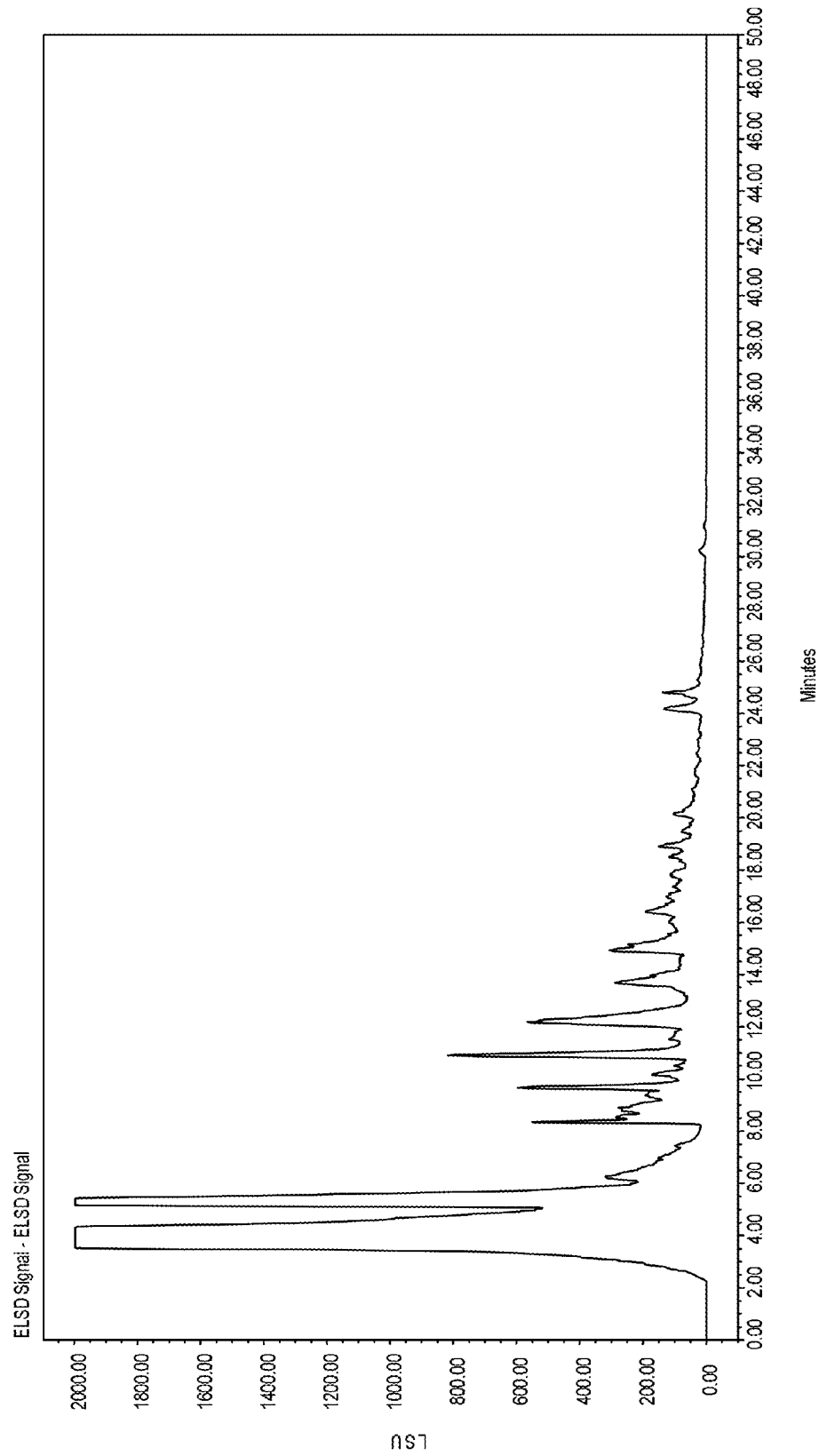
FIG. 8 shows a chromatographic fingerprint of the initial composition before the fermentation step.

The various dry extracts were then mixed in a volume of water. The solution obtained was analysed and then identified by NMR, HPLC, HPLC-MS techniques, in order to obtain a chromatographic footprint, as illustrated in FIG. 8.

EXAMPLE 9

Composition of Example 8 after Fermentation

Prior to incubation, the composition resulting from example 8 was diluted in water to which glucose had been added at a concentration of 50 g/L and ammonium nitrate at a concentration of 20 g/L. The composition obtained was then subjected to bioconversion by controlled fermentation using the strain *Beauveria bassiana* ATCC 7159.

This strain was cultivated beforehand in a culture medium composed of (per litre of water) 0.5 g/L $KH_2PO_4$; 1 g/L $KH_2PO_4$; 1 g/L $MgSO_4$; 2 g/L $NaNO_3$; 0.5 g/L KCl; 0.02 g/L $FeSO_4$; 30 g/L glucose and 10 g/L of corn steep liquor (Rocket). The culture was then agitated at 200 rotations per minute, for 72 hours at 27° C. It was then filtered by non-sterile methods on a filter paper to separate the fungal biomass from the culture medium. The fungal biomass was then washed thoroughly with water and incubated with 60 g of fresh biomass per litre of incubation, that contained 37.5 g of glucose and 15 g of ammonium nitrate.

After incubation, this seeded composition was agitated at 200 rpm for 7 days at a temperature of 27° C.

After 7 days, the incubation medium was filtered on a filter paper, the samples for HPLC assay were also filtered using a 0.45 micron filter (Ait-France, ref: SFNY 013045N).

Figure 9:
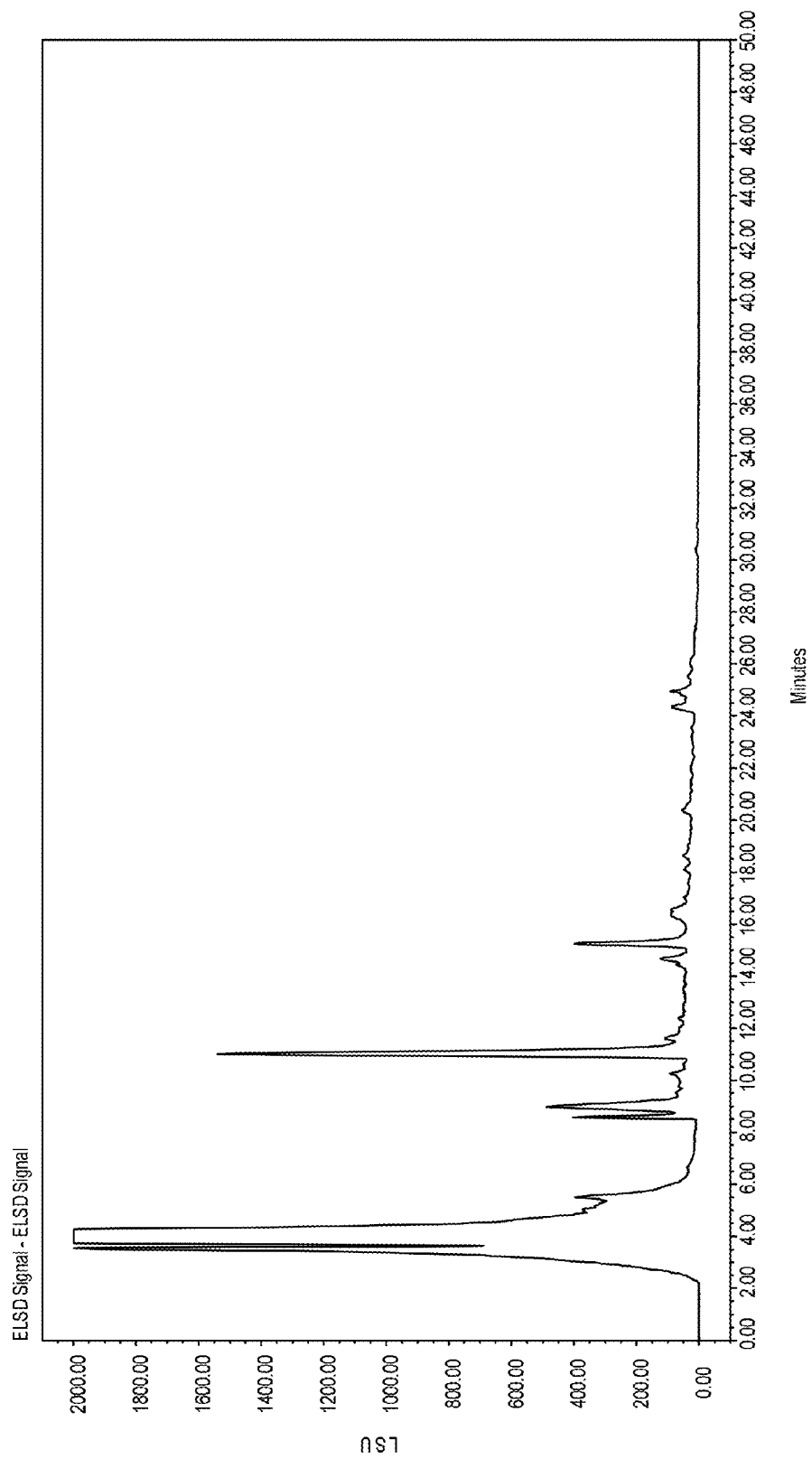
FIG. 9 shows a chromatographic fingerprint of the composition according to example 8 after 7 days fermentation of this composition in the presence of the strain *Beauveria bassiana* ATCC 7159.

A brownish solution was obtained which was then analysed and identified by NMR, HPLC, HPLC-MS techniques, in order to obtain a chromatographic footprint, as shown in FIG. 9.

The samples obtained were analysed as in example 1.

EXAMPLE 10

Composition Containing Plant Extracts before Fermentation

A composition containing an extract of *Withania Somnifera* at a concentration of 20 g/L, of *Emblica officinalis* at a concentration of 15 g/L, of *Bacopa monnieri* at a concentration of 15 g/L, of *Punica granatum* at a concentration of 10 g/L, of *Curcuma longa* at a concentration of 20 g/L, of *Piper longum* at a concentration of 0.03 g/L, and of *Calendula officinalis* at a concentration of 10 g/L, was prepared from plants.

The plant material was briefly ground. Each plant was chopped independently of other plants, using grinders of the HGB50E-Blender type, so as to obtain the finest powders possible, of the order of 80 microns in diameter.

Extractions were then performed for each plant extract by maceration. During such extraction by maceration, the temperature is between 40° C. and 60° C. and the pressure is 100 bar during the two 1-hour cycles. After extraction, the heterogeneous solutions obtained were filtered on filter paper with a thickness of 870 μm and a diameter of 170 mm. The solutions obtained were collected and concentrated under reduced pressure using a BUCHI R-220-SE Rotavapor to provide an aqueous solution. These solutions were frozen at −80° C., before being deposited in a freeze dryer at −55° C. and under a pressure of 0.1 mbar (Edwards Modulyo Freeze Dryer) to produce the dried extracts.

Figure 10:
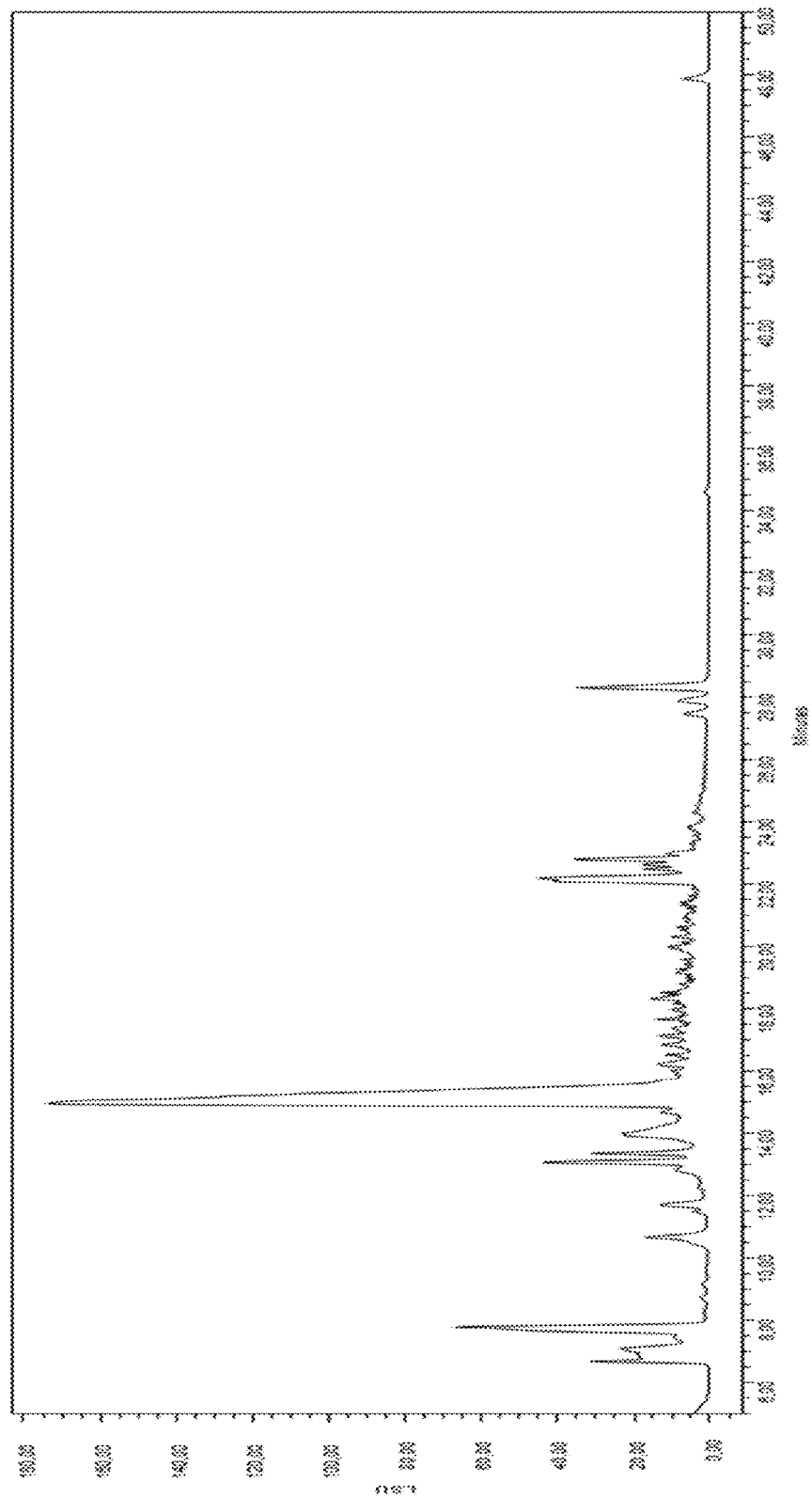
FIG. 10 shows a chromatographic fingerprint of another initial composition before the fermentation step.

The various dry extracts were then mixed in a volume of water. The solution obtained was analysed and then identified by NMR, HPLC, HPLC-MS techniques, in order to obtain a chromatographic footprint, as illustrated in FIG. 10.

EXAMPLE 11

Composition of Example 10 after Fermentation

Prior to incubation, the composition resulting from example 10 was diluted in water to which glucose had been added at a concentration of 50 g/L and ammonium nitrate at a concentration of 20 g/L. The composition obtained was then subjected to bioconversion by controlled fermentation using the strain *Beauveria bassiana* ATCC 7159.

This strain was cultivated beforehand in a culture medium composed of (per litre of water) 0.5 g/L $KH_2PO_4$; 1 g/L $KH_2PO_4$; 1 g/L $MgSO_4$; 2 g/L $NaNO_3$; 0.5 g/L KCl; 0.02 g/L $FeSO_4$; 30 g/L glucose and 10 g/L of corn steep liquor (Rocket). The culture was then agitated at 200 rotations per minute, for 72 hours at 27° C. It was then filtered by non-sterile methods on a filter paper to separate the fungal biomass from the culture medium. The fungal biomass was then washed thoroughly with water and incubated with 60 g of fresh biomass per litre of incubation, that contained 37.5 g of glucose and 15 g of ammonium nitrate.

After incubation, this seeded composition was agitated at 200 rpm for 7 days at a temperature of 27° C.

After 7 days, the incubation medium was filtered on a filter paper, the samples for HPLC assay were also filtered using a 0.45 micron filter (Ait-France, ref: SFNY 013045N).

Figure 11:
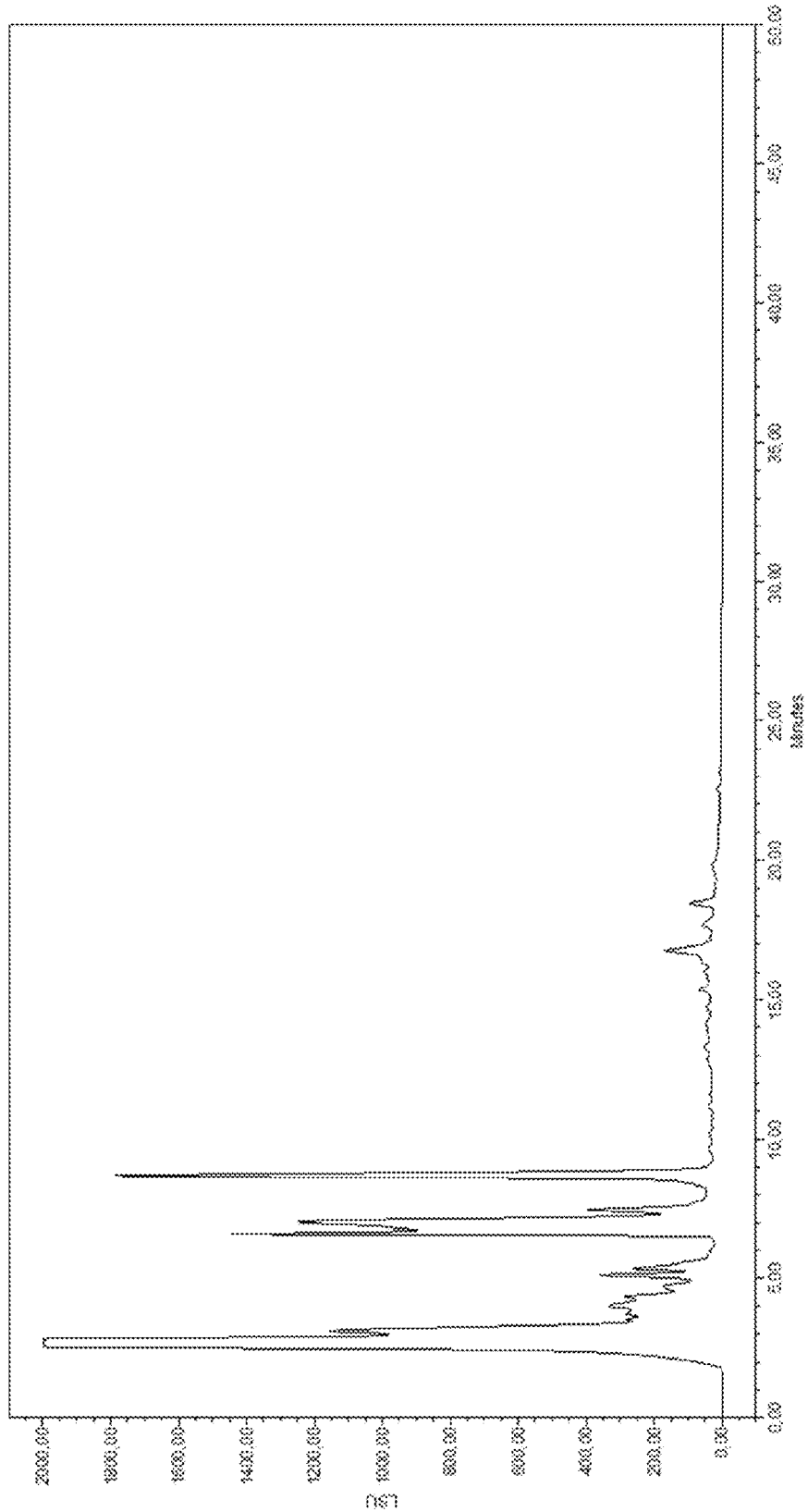
FIG. 11 shows a chromatographic fingerprint of the composition according to example 10 after 7 days fermentation of this composition in the presence of the strain *Beauveria bassiana* ATCC 7159.

A brownish solution was obtained which was then analysed and identified by NMR, HPLC, HPLC-MS techniques, in order to obtain a chromatographic footprint, as shown in FIG. 11.

The samples obtained were analysed as in example 1.

EXAMPLE 12

A Composition According to the Invention before Fermentation

The composition is composed of *Withania somnifera* at a concentration of 40 g/L, *Emblica officinalis* at a concentration of 30 g/L, and *Bacopa monnieri* at a concentration of 30 g/L.

Figure 12:
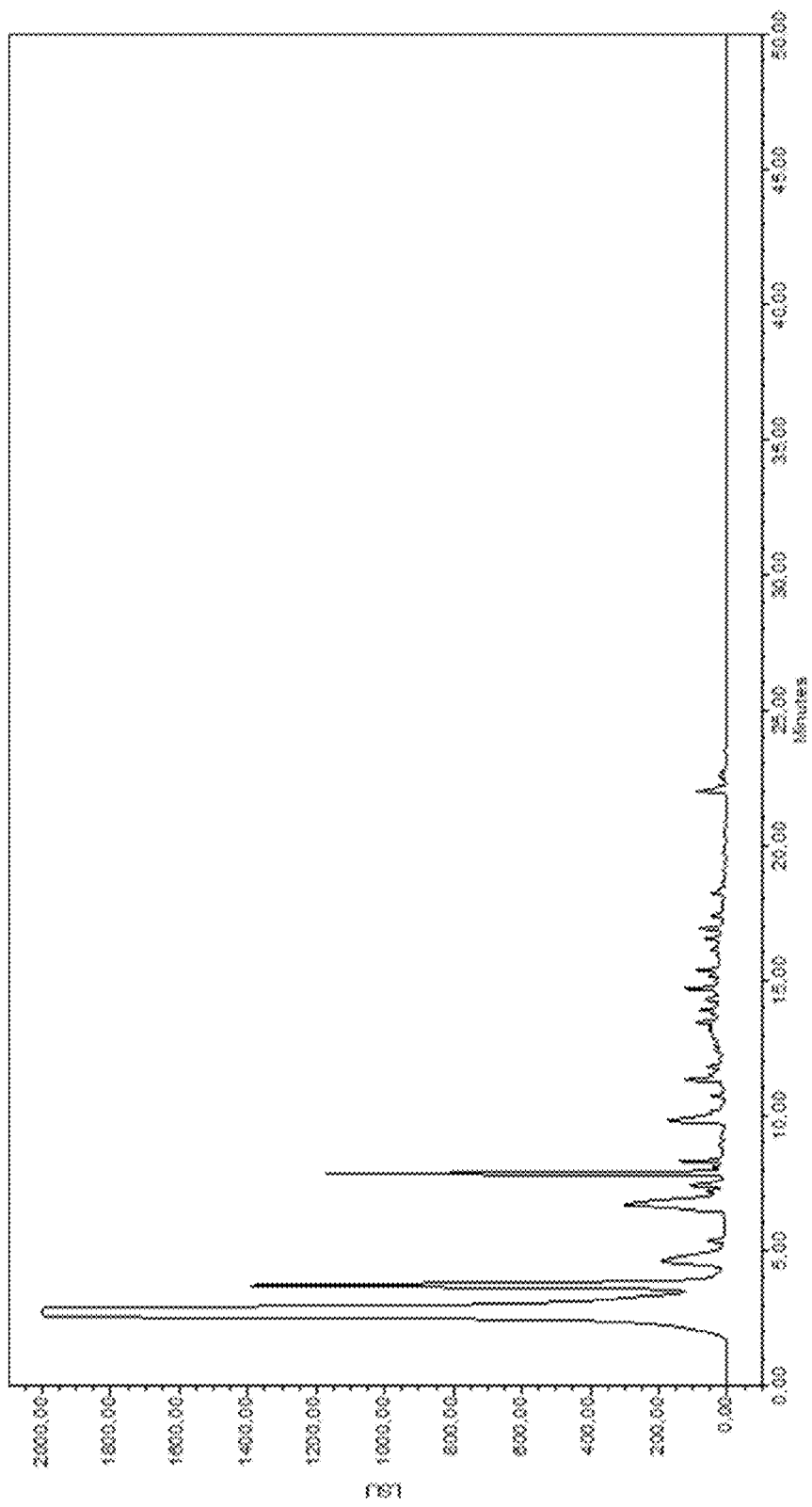
FIG. 12 shows a chromatographic fingerprint of the composition according to example 12.

It has been analysed by the same techniques as in the previous example (FIG. 12).

EXAMPLE 13

Characterisation of Elements of the Composition According to Example 12

Figure 13:
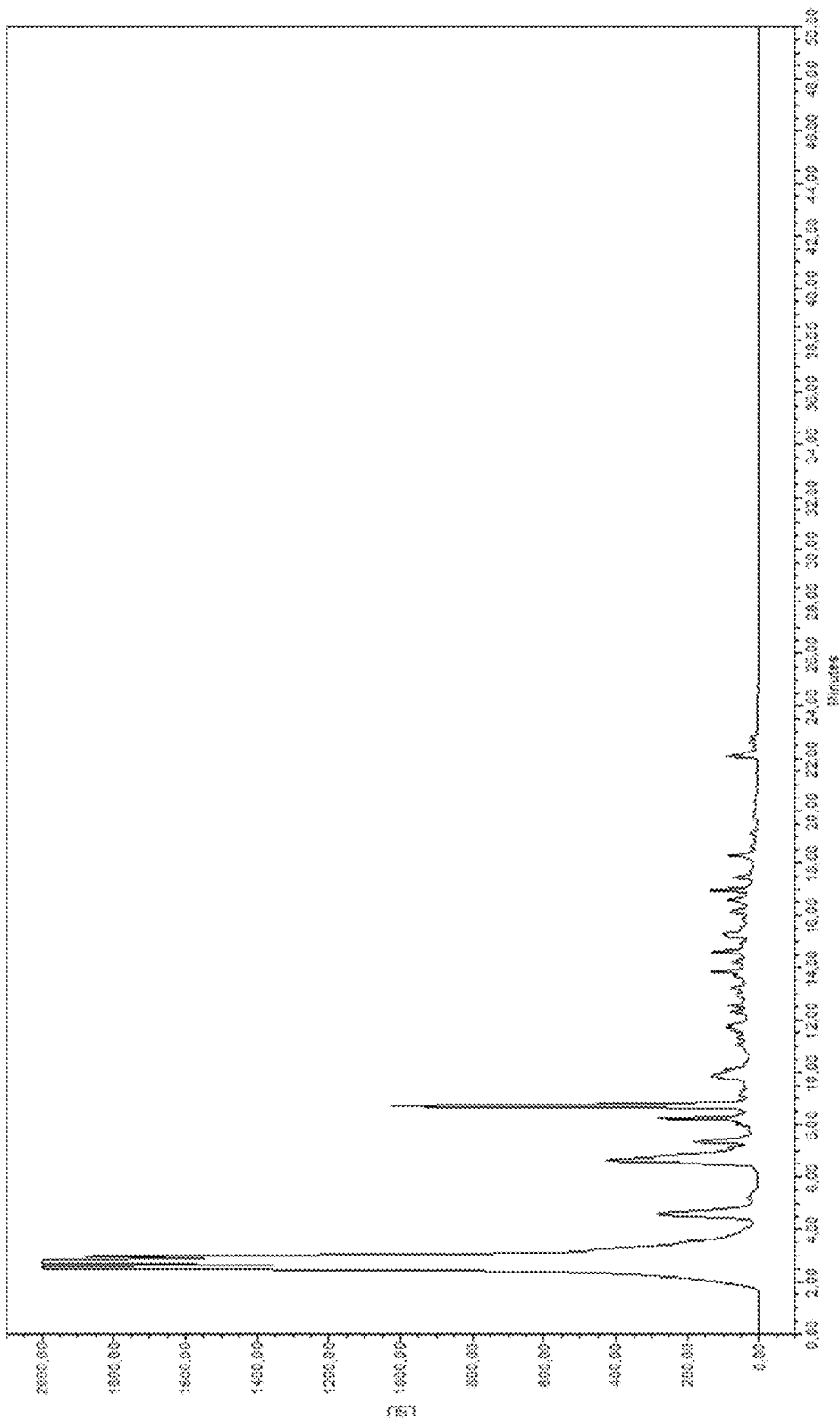
FIG. 13 shows a chromatographic fingerprint of the composition according to example 13.

After the fermentation step, the composition of example 12 was characterised more precisely (FIG. 13).

The incubation medium was filtered on a filter paper, the samples for HPLC analysis were also filtered using a 0.45 micron filter (Ait-France, ref: SFNY 013045N) prior to injection for analysis. The markers identified in the composition were Withanoside IV, Withanoside VI, Bacoside A3, Bacopaside X, Bacopasaponin C, as well as gallic acid and its derivative.

Gallic acid and its osidic derivative

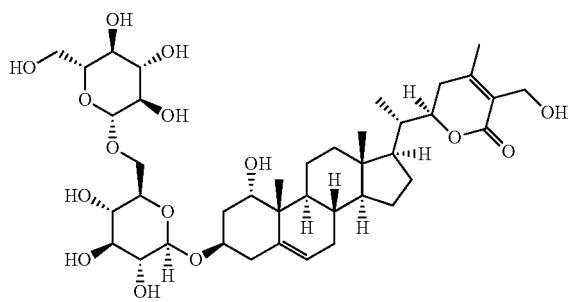

Withanoside IV
Chemical Formula: $C_{40}H_{62}O_{15}$
Molecular Weight: 782.91

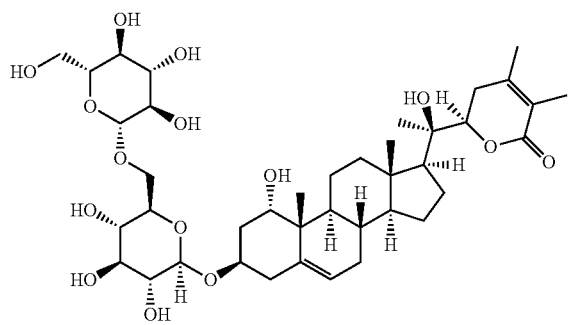

Withanoside VI
Chemical Formula: $C_{40}H_{62}O_{15}$
Molecular Weight: 782.91

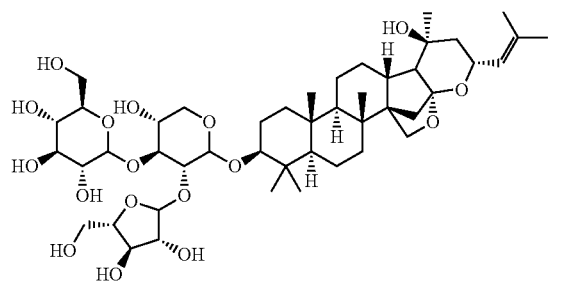

Bacopaside X
Chemical Formula: $C_{46}H_{74}O_{17}$
Molecular Weight: 899.07

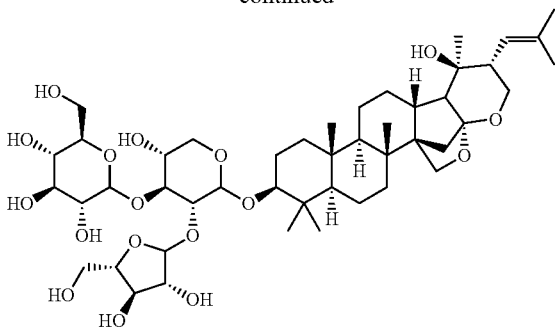

Bacopasaponin C
Chemical Formula: $C_{46}H_{74}O_{17}$
Molecular Weight: 899.07

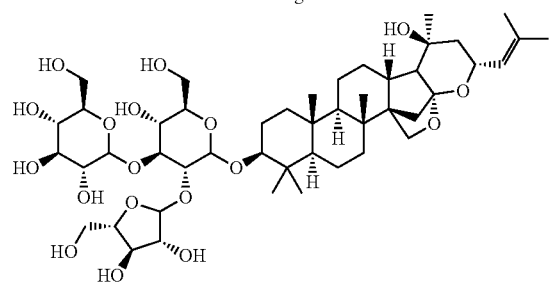

Bacoside A3
Chemical Formula: $C_{47}H_{76}O_{18}$
Molecular Weight: 929.10

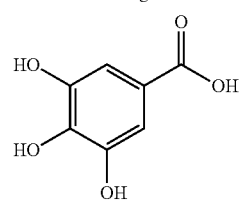

Chemical Formula: $C_7H_6O_5$
Molecular Weight: 170.12

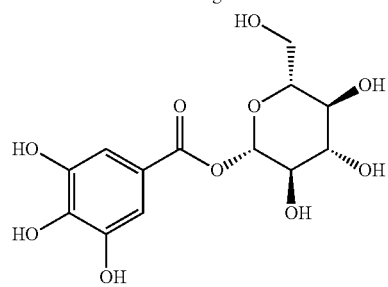

Chemical Formula: $C_{13}H_{16}O_{10}$
Molecular Weight: 332.26

EXAMPLE 14

Composition According to the Invention before Fermentation

Figure 14:
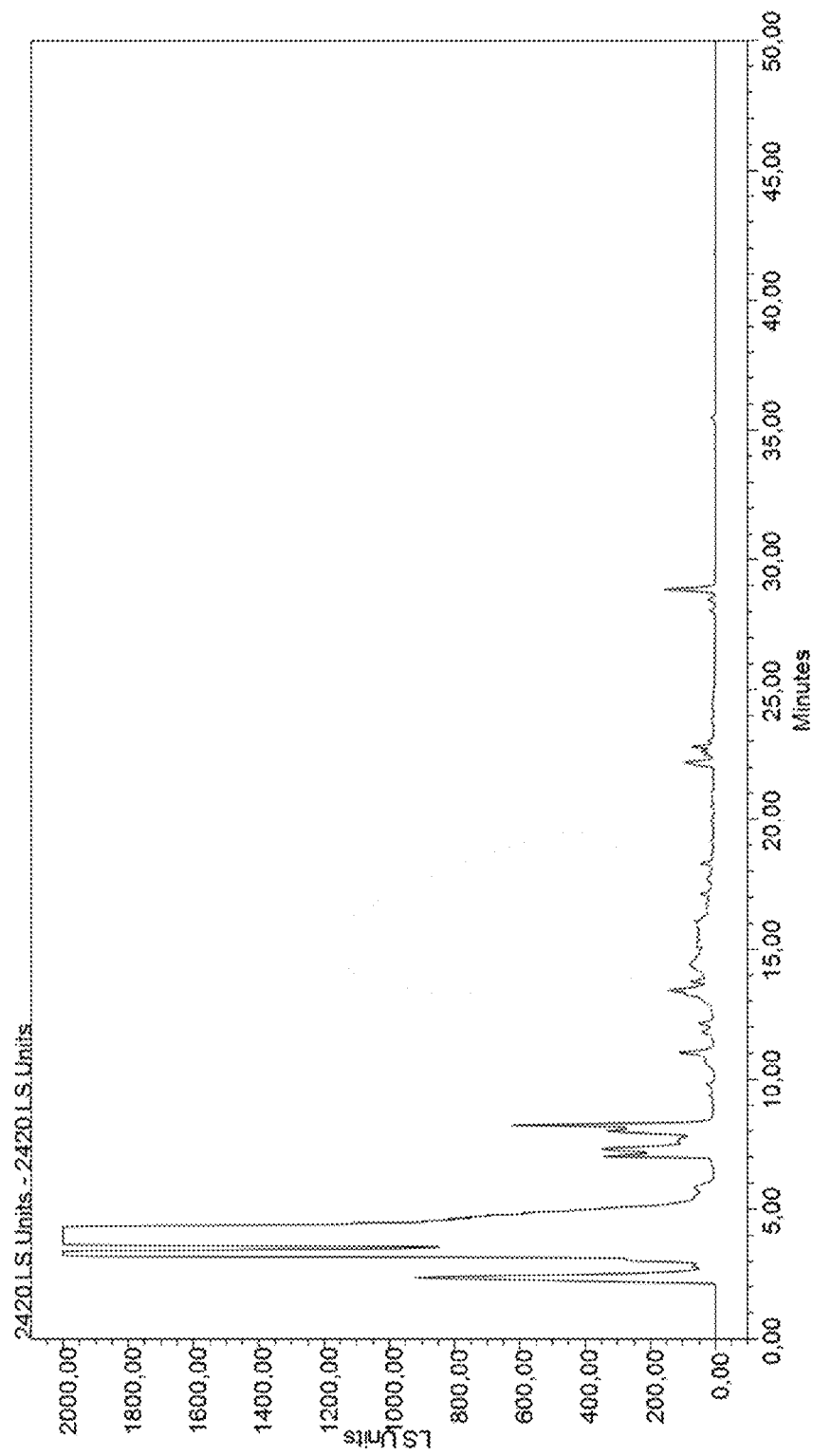
FIG. 14 shows a chromatographic fingerprint of the composition according to example 14.

The preparation is composed of *Withania somnifera* at a concentration of 20 g/L, *Emblica officinalis* at a concentration of 15 g/L, *Bacopa monnieri* at a concentration of 15 g/L, *Piper longum* at a concentration of 20 mg/L, and *Curcuma* at a concentration of 20 g/L (FIG. 14).

EXAMPLE 15

Anti-Angiogenic Properties of the Compositions of Examples 10 and 11 (before and after Fermentation)

Biological tests in ovo, according to the chicken chorio-allantoic membrane (CAM) technique were conducted using the composition of example 10 and of example 11.

The eggs were supplied by EARL Les Bruyères, DANGERS. The eggs used for the tests were delivered on the day of laying, or no later than the day following the day of laying. The eggs were obtained from a cross of JA57 hens and I66 cocks, which are normally intended to produce I657 chicks.

Two sets of 12 eggs were treated, 7 days after fertilisation.
The first set had 40 µL of the composition from example 10 administered onto the CAM.
The second set had 40 µL of the composition from example 11 administered onto the CAM.

Photographs were taken of the CAM before administration, and at 24 h, 48 h and 72 h after administration of the composition, in order to follow the development of vascularisation At 24 hours, 100% of the embryos from the first set were dead (FIGS. 15A to 15D) following severe bleeding, probably due to the toxicity of the composition resulting in destruction of the CAM.

After 78 hours, only two embryos from the 12 of the second set are dead. In addition, the fermented composition of example 1 led to a very sharp reduction in the vascular network among all the eggs handled, as observed in FIGS. 16A to 16D.

The composition according to the invention therefore has anti-vascularising properties.

In addition, this test evidences the detoxification in ovo of the composition obtained according to the method of the invention.

EXAMPLE 16

Evaluation of Compound of the Invention as Modulator of VEGF Expression/Secretion The compounds of examples 8 and 9 were dissolved in DMSO at a stock solution of 10 mg/mL. Starting working concentration was that of 500 ng/mL in DMSO. Avastin (Bevacizumab®, ROCHE, Germany) is used as a positive control. Avastin is a humanized monoclonal antibody to VEGF that inhibits VEGF-receptor interaction. Given its known interaction with VEGF and the induced downstream effects to its receptor, Avastin was used as a positive control for the demonstration of compounds' effects on VEGF expression/secretion.

The tests were performed in endothelial cells, namely replicating human umbilical vein endothelial cells (HUVEC) or in replicating (young) human foreskin fibroblasts (BJ). Both cell types were cultured at 37° C., 5% $CO_2$ in ambient oxygen concentration. HUVEC cells were cultured in Medium 199 (GIBCO, France) including 15% Fetal Bovine Serum (FBS) and Large Vessel Endothelial Supplement (LVES) 1× (GIBCO). Human newborn foreskin (BJs) fibroblasts were obtained from the American Tissue Culture Collection and were maintained in Dulbecco's modifies Eagle's medium (Gibco Life Technologies), supplemented with 10% (v/v) fetal bovine serum, 2 mM glutamine and 1% non-essential amino acids. In all experimental procedures, proliferating cells were subcultured at a split ratio 1:2 (when confluent) by using a trypsin/EDTA solution (Gibco Life Technologies).

Viability after cell exposure to the compounds or Avastin was determined by the 3-(4,5-dimethylthiazol-2-yl)-2,5 diphenyltetrazolium bromide (MTT) assay (Sigma, France). Used concentrations of the compounds were those of 500 ng/mL up to 10 µg/mL, while concentration of Avastin was that of 125 and 250 µg/mL. Cell were plated in 96-well plates and the day after, were treated with the compounds or Avastin. Then, at 24-hrs post treatment cells' metabolic activity (indicative of cell survival) was measured by the addition of the MTT compound. Specifically, following the completion of the treatment the medium was replaced by MTT dissolved at a final concentration of 1 mg/mL in serum-free, phenol red-free medium. The reduction of the dye by the living cells was allowed to take place for 3-4 h. The MTT solution was discarded and isopropanol was added to dissolve the formazan crystals. The absorbance of the solution was measured at 570 nm wavelength. Survival of control cells was arbitrarily set to 100%. For cell proliferation analyses, seeded cells were viewed-photographed and counted following a period of 96 hrs exposure to the compounds. Briefly, cells were plated in 96-well plates and were left to replicate for 96 hrs in the presence (or absence) of the compounds. Cells' morphology as well as cells' number was then recorded. Cells morphology during treatment was recorded by phase contrast imaging using an Eclipse TS-100F NIKON inverted microscope, while cell number was measured in a cell coulter counter [Countess, Automated Cell Counter (Invitrogen)].

VEGF-165 levels in cell culture supernatant were measured by using the Human VEGF Quantikine ELISA kit (DVE00, R&D Systems); a standard curve was also established as per manufacturer instructions.

To analyze the rate of protein secretion after the addition of the compounds (or in control samples), total cell culture supernatants were collected.

Samples were prepared on ice in NP-40 lysis buffer [150 mM NaCl, NP-40, 1.0%, Tris-Cl 50 mM, pH 8.0] containing protease inhibitors (Phosphatase Inhibitor Cocktail 1 [microcystinLR, cantharidin, (−)-p-bromotetramisole (P2850, SIGMA; France)], Phosphatase Inhibitor Cocktail 2 [sodium orthovanadate, sodium molybdate, sodium tartrate, imidazole (P5726,SIGMA)] and Protease Inhibitor [AEBSF, aprotinin, bestatin, E-64, leupeptin, pepstatin A (P8340, SIGMA)].

Supernatants were centrifuged for 10 min at 19 000 g (4° C.), adjusted by Bradford (Bio-Rad); and were then analyzed by SDS-PAGE to fractionate cell or supernatant protein and immunoblotting using antibodies in order to differentially measure protein expression in the samples analyzed.

Primary antibodies used were against VEGF of human origin [147 (sc-507) or C-1 (7269) from Santa Cruz, Germany]. Secondary antibodies were goat anti-rabbit IgG-HRP sc-2004, goat anti-mouse IgG-HRP sc-2005 (Santa Cruz, Germany). Primary and secondary antibodies were applied for 1 h at room temperature.

Immunoblots were developed using the enhanced chemiluminescence reagent kit "Clarity Western ECL Substrate" (170-5061, BIORAD, USA).

Blots quantification was performed by scanning densitometry.

For gene expression analyses, new primers were designed for the VEGF-A, HIF-1A and MMP-2 genes, as these genes are, likely, activated upon reduced VEGF extracellular signaling.

Sequence of RT-PCR primers is as follows:

```
H-VEGFA-Forward
CGAGGCAGCTTGAGTTAAACG

H-VEGFA-Reverse
GGTGAGAGATCTGGTTCCCG

H-HIF1A-Forward
GCCAGACGATCATGCAGCTA

H-HIF1A-Reverse
ATCCATTGATTGCCCCAGCA

H-MMP2-Forward
ATAACCTGGATGCCGTCGTG

H-MMP2-Reverse
AGCCTAGCCAGTCGGATTTG

H-B2M-Forward
ACT-GAA-TTC-ACC-CCC-ACT-GA

H-B2M-Reverse
AAG-CAA-GCA-AGC-AGA-ATT-TGG

H-HMBS-Forward
AAG-AGA-CCA-TGC-AGG-CTA-CCA

H-HMBS-Reverse
ACA-AGT-TGG-CCA-GGC-TGA-TG
```

Samples were analyzed by Quantitative Real Time PCR analyses after exposing HUVEC cells for 24 hrs to the compounds of examples 8 and 9. For normalization, two different genes were used, namely B2M and HMBS.

The human B2M or beta-2-microglobulin encodes a serum protein found in association with the major histocompatibility complex (MEW) class I heavy chain on the surface of nearly all nucleated cells.

The HMBS or hydroxymethylbilane synthase encodes a member of the hydroxymethylbilane synthase superfamily. The encoded protein is the third enzyme of the heme biosynthetic pathway and catalyzes the head to tail condensation of four porphobilinogen molecules into the linear hydroxymethylbilane.

Results

Figure 17:
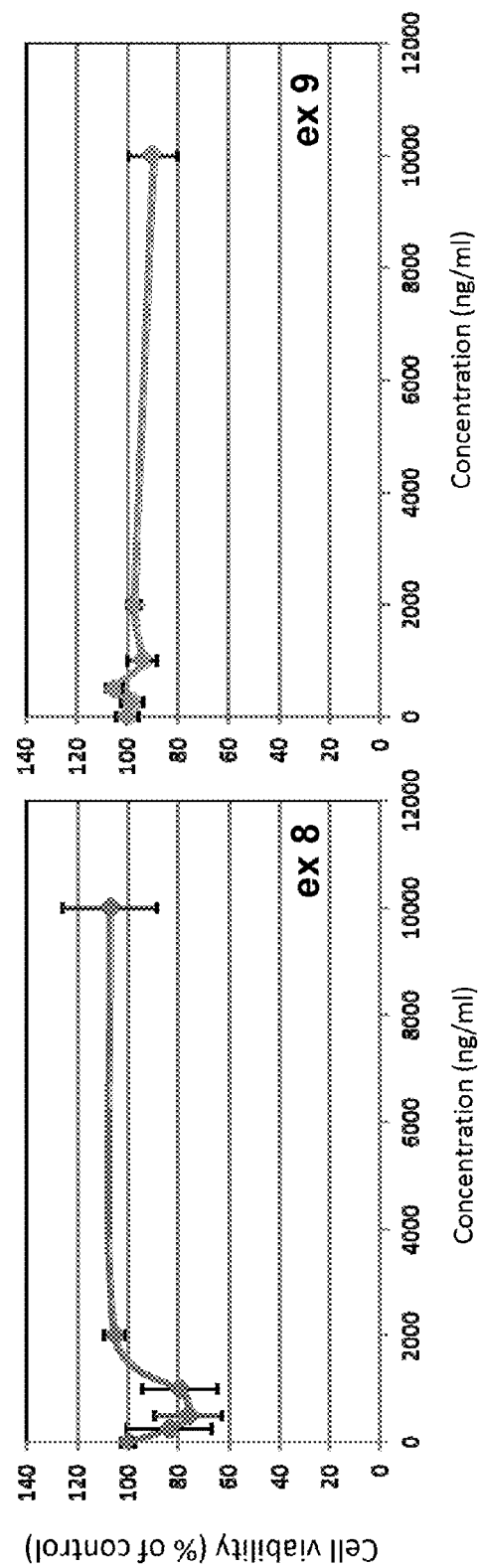
FIGS. 17 and 21 show the absence of toxicity of the compounds tested on either BJ cells (FIG. 17) or on HUVEC cells (FIG. 21) with either the composition of example 8 or example 9.
Figure 21:
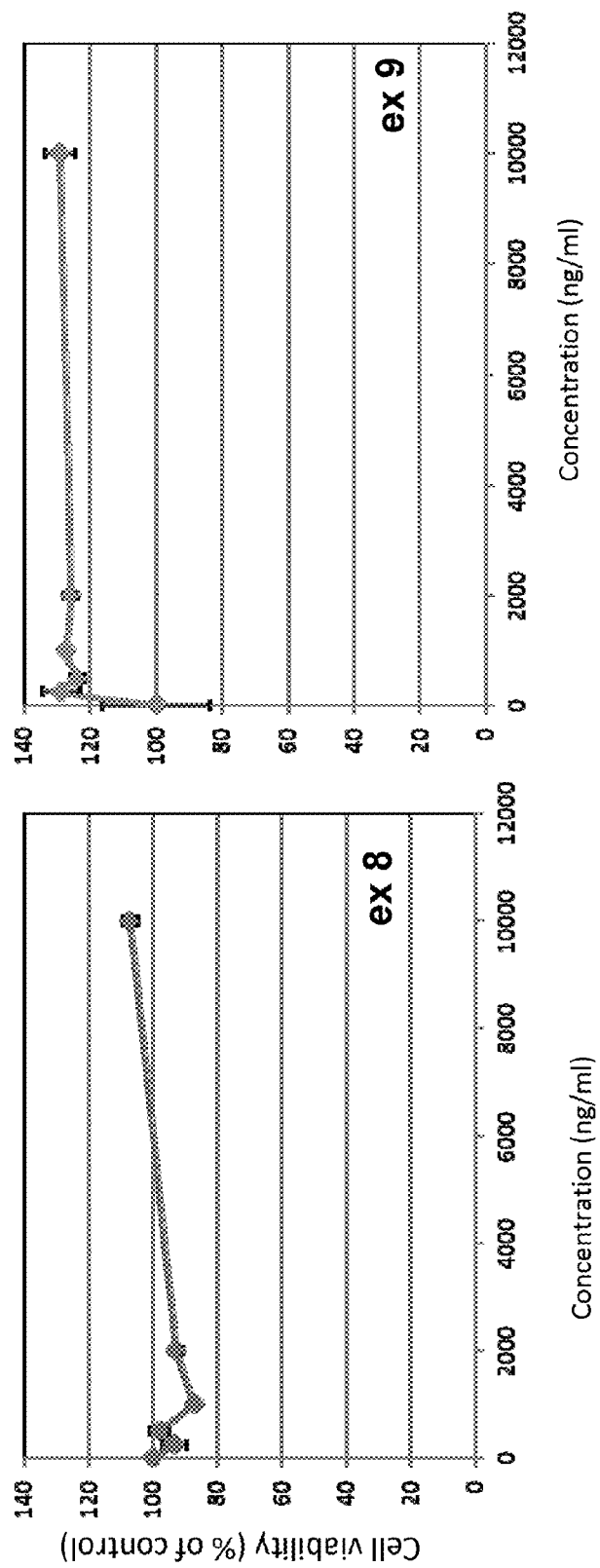

None of the compounds was toxic in either BJs (FIG. 17) or HUVEC (FIG. 21) cells.

Figure 18:
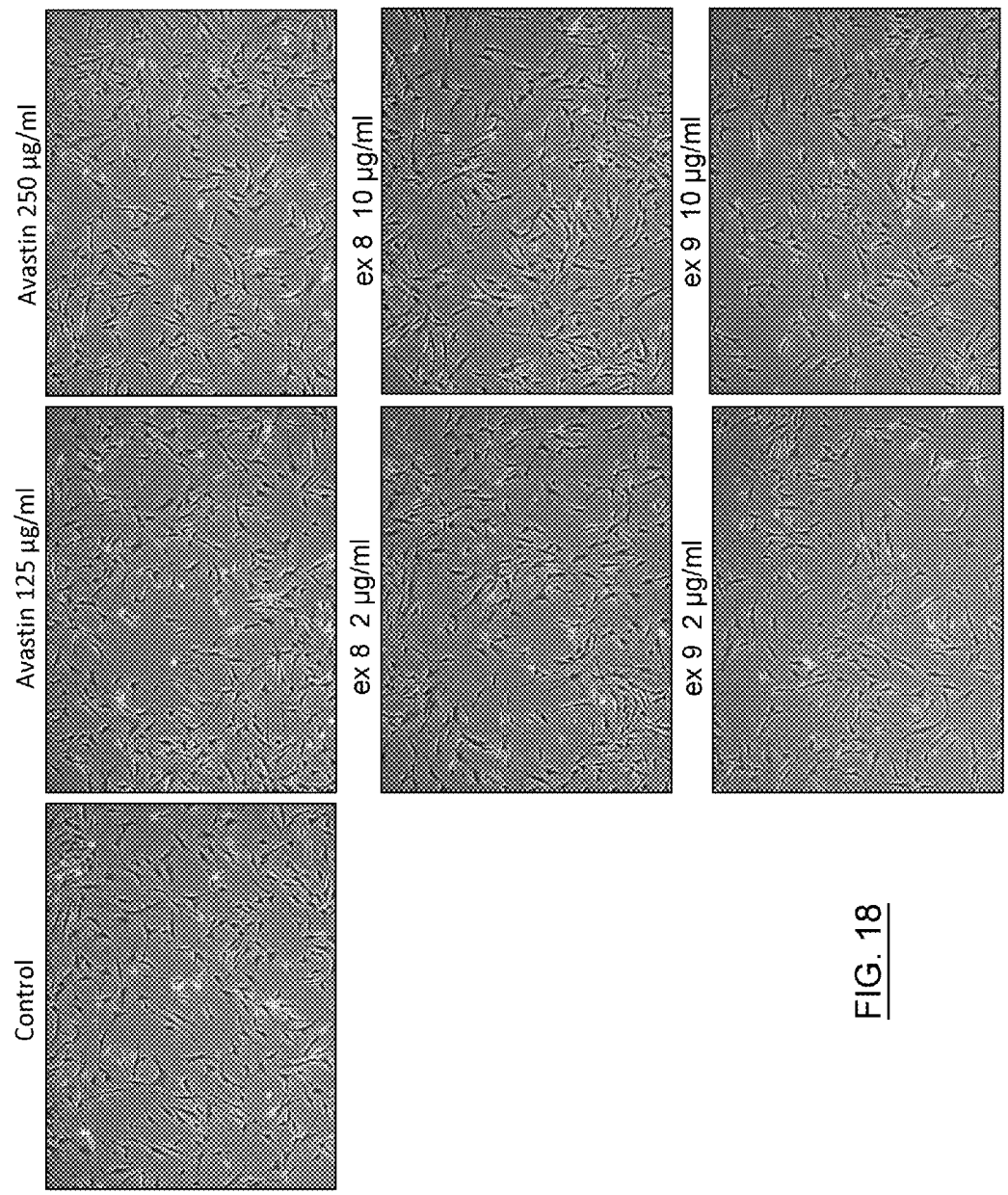
FIGS. 18 and 22 show the proliferation of BJ cells (FIG. 18) or HUVEC cells (FIG. 22) with avastin, the composition of example 8 or the composition of example 9.
Figure 22:
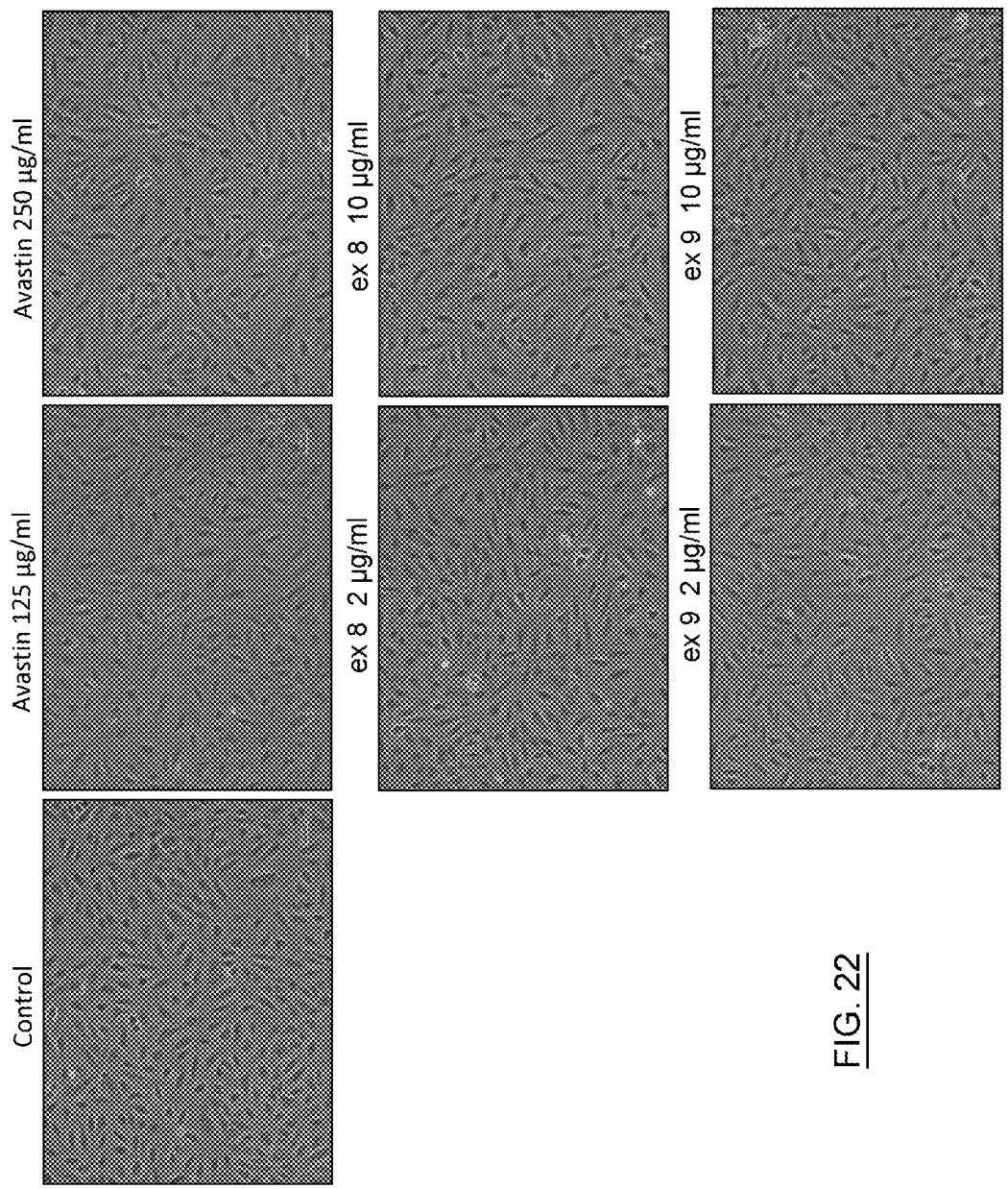

Neither the compound of example 8, nor the compound of example 9 affects proliferation of BJs (FIG. 18) or HUVEC (FIG. 22) cells.

Figure 19:
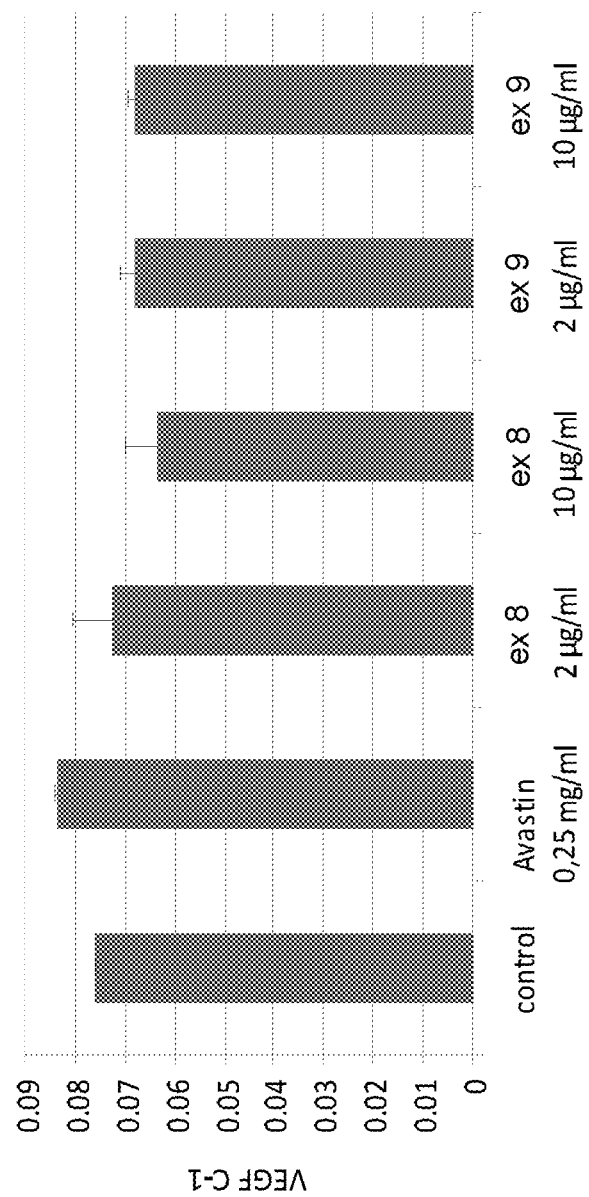
FIGS. 19 and 23 show the amount of extracellular VEGF C-1 in BJ cells (FIG. 19) or HUVEC cells (FIG. 23) with avastin, the composition of example 8 or the composition of example 9.
Figure 20:
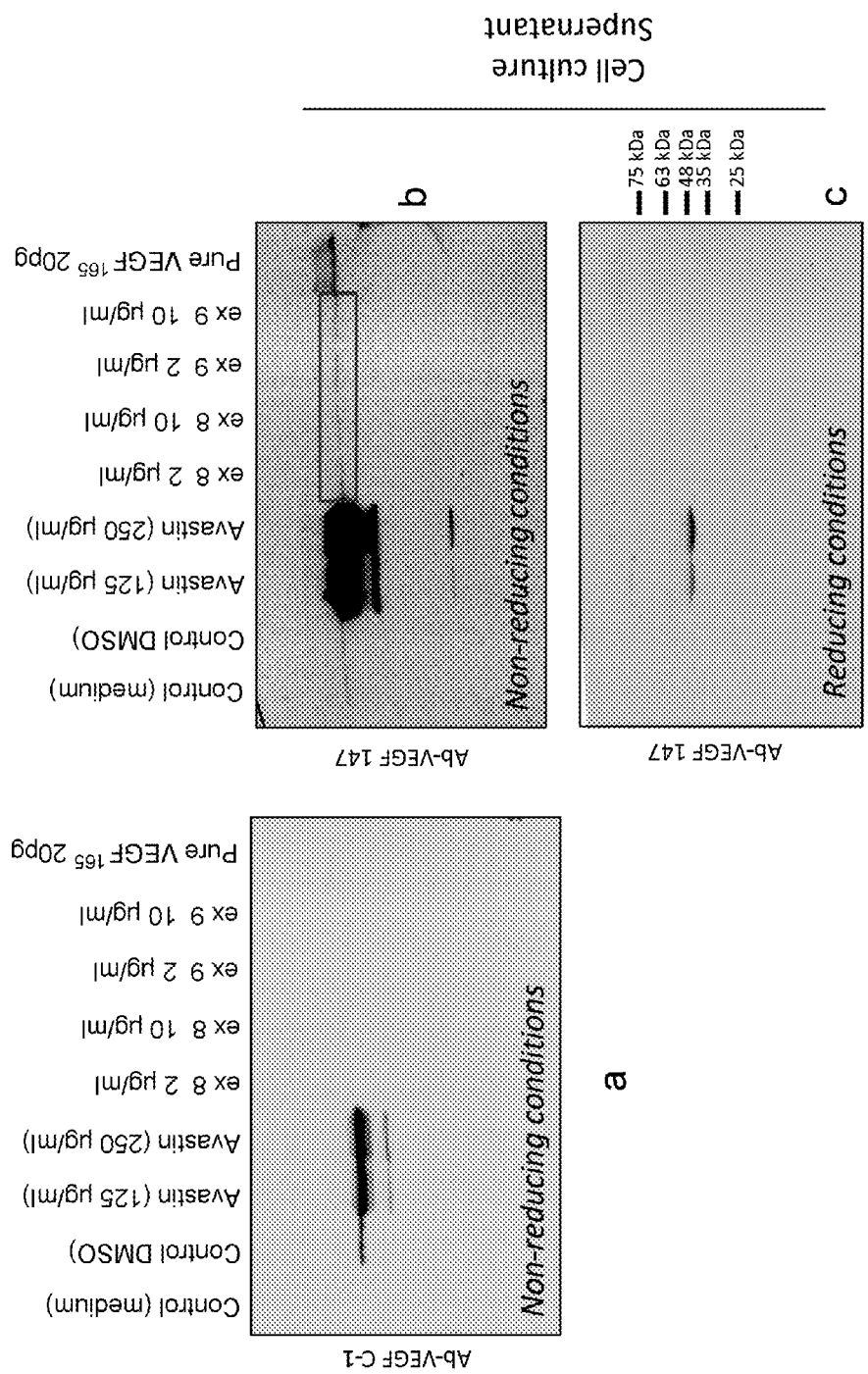
FIGS. 20 and 24 show the amount of VEGF in BJ cell culture supernatants (FIG. 20) or HUVEC cell culture supernatants (FIG. 24) with avastin, the composition of example 8 or the composition of example 9. Two antibodies are used, ab-VRGF C-1 and ab VEGF 147. The immunoblots of FIGS. 20 and 24 a) and b) are in non-reducing conditions.
Figure 23:
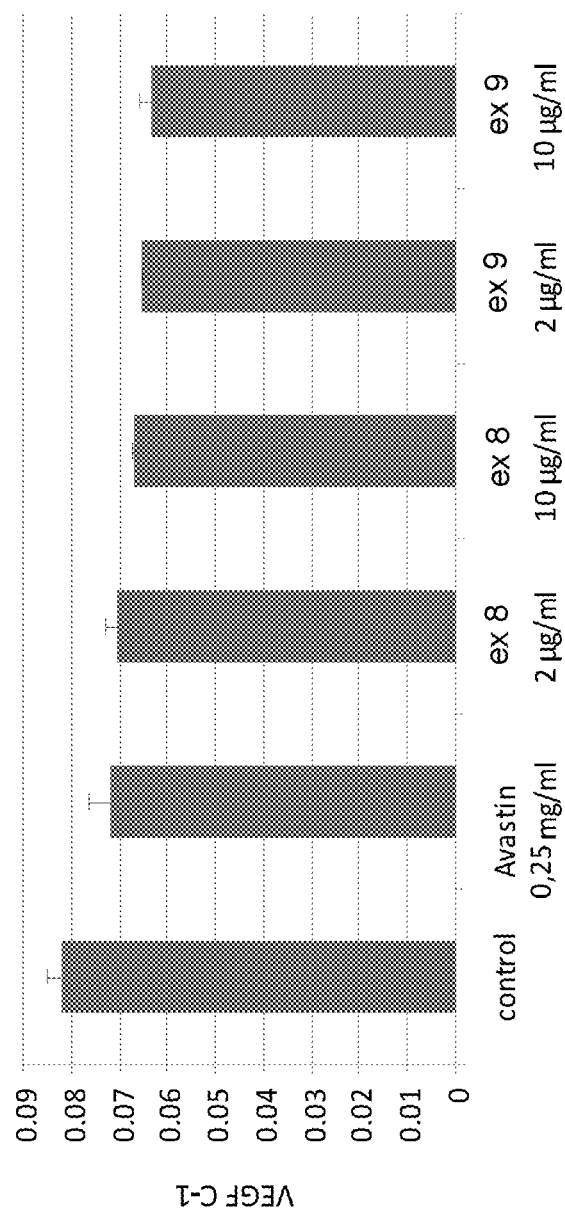
Figure 24:
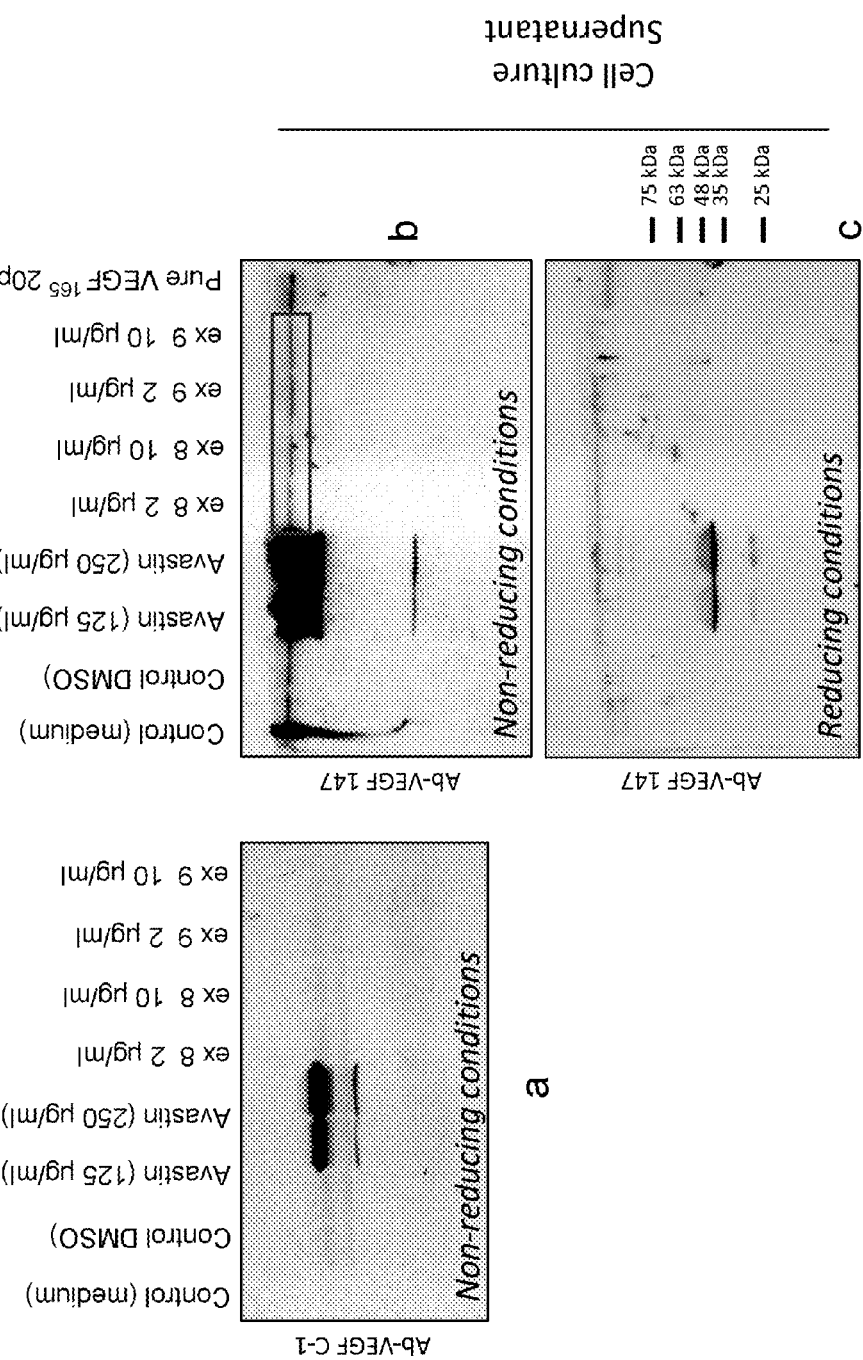
Figure 25:
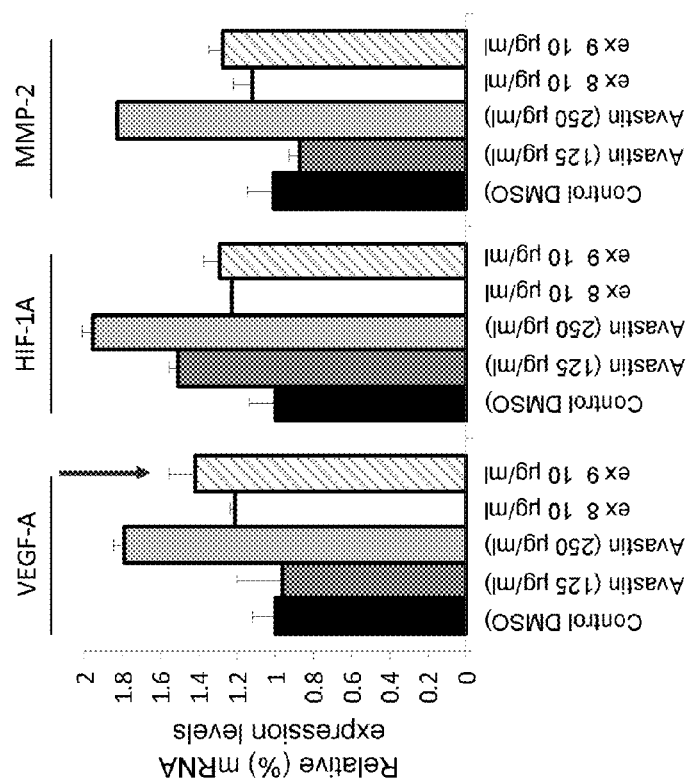
FIGS. 25 and 26 show the relative mRNA expression levels in BJ cells (FIG. 25) or HUVEC cells (FIG. 26) with avastin, the composition of example 8 or the composition of example 9, in presence either of VEGF-A, HIF-1A or MMP-2. In these experiments, the normalizer is the B2M gene.
Figure 26:
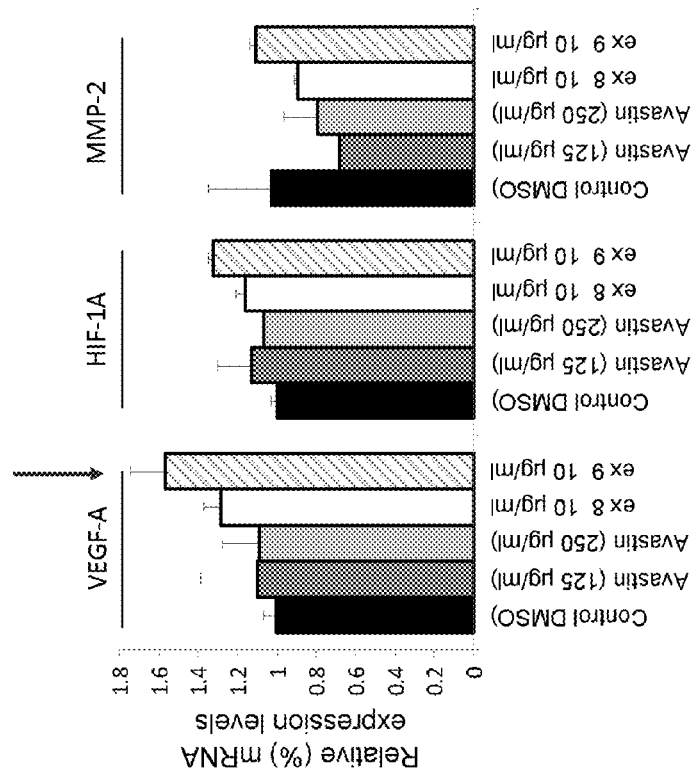

In both cell lines, no significant differences in extracellular VEGF C-1 (by using an ELISA kit) (FIGS. 19, 23) or in higher VEGF levels at the cell culture supernatant (immunoblotting analyses; FIGS. 20, 24) could be detected.

the avastin-like gene expression profiles are more enhanced by the compound of example 9 than by the compound of example 8 (FIGS. 25, 26).

The compound of example 9 (which is detoxified), has a significant effect on the VEGF regulatory pathway, contrary to compound of example 8 (before detoxification).

The results show that this detoxified compound exerts an Avastin-like effect on HUVEC cells.

While illustrative embodiments have been illustrated and described, it will be appreciated that various changes can be made therein without departing from the spirit and scope of the invention.

The invention claimed is:

1. A method for obtaining a plant extract comprising the following steps:
   Production of an extract of *Withania somnifera*
   Fermentation of the extract of *Withania somnifera* by its incubation with a filamentous fungus of the family Cordycipitaceae in a suitable environment.

2. The method for obtaining an extract according to claim 1, in which the fungus from the family Cordycipitaceae is from the genus *Beauveria*.

3. The method for obtaining an extract according to claim 1, comprising, after fermentation, a filtration step of the culture medium.

4. The method for obtaining an extract according to claim 1, comprising, after fermentation, a sterilisation step of the culture medium.

5. The method for obtaining an extract according to claim 1, comprising a dehydration step of the culture medium, after fermentation.

6. The method for obtaining an extract according to claim 1, in which an extract of *Emblica officinalis* and an extract of *Bacopa monnieri* are added to the *Withania somnifera* extract before performing fermentation of said extracts with said filamentous fungus in a suitable medium.

7. The method for obtaining an extract according to claim 2, wherein the fungus is *Beauveria bassiana*.

* * * * *

SEQUENCE LISTING

```
<160> NUMBER OF SEQ ID NOS: 10

<210> SEQ ID NO 1
<211> LENGTH: 21
<212> TYPE: DNA
<213> ORGANISM: Homo sapiens

<400> SEQUENCE: 1
cgaggcagct tgagttaaac g                                    21

<210> SEQ ID NO 2
<211> LENGTH: 20
<212> TYPE: DNA
<213> ORGANISM: Homo sapiens

<400> SEQUENCE: 2
ggtgagagat ctggttcccg                                      20

<210> SEQ ID NO 3
<211> LENGTH: 20
<212> TYPE: DNA
<213> ORGANISM: Artificial Sequence
<220> FEATURE:
<223> OTHER INFORMATION: Synthetic

<400> SEQUENCE: 3
gccagacgat catgcagcta                                      20

<210> SEQ ID NO 4
<211> LENGTH: 20
<212> TYPE: DNA
```

```
<213> ORGANISM: Artificial Sequence
<220> FEATURE:
<223> OTHER INFORMATION: Synthetic

<400> SEQUENCE: 4
atccattgat tgccccagca                                               20

<210> SEQ ID NO 5
<211> LENGTH: 20
<212> TYPE: DNA
<213> ORGANISM: Artificial Sequence
<220> FEATURE:
<223> OTHER INFORMATION: Synthetic

<400> SEQUENCE: 5
ataacctgga tgccgtcgtg                                               20

<210> SEQ ID NO 6
<211> LENGTH: 20
<212> TYPE: DNA
<213> ORGANISM: Artificial Sequence
<220> FEATURE:
<223> OTHER INFORMATION: Synthetic

<400> SEQUENCE: 6
agcctagcca gtcggatttg                                               20

<210> SEQ ID NO 7
<211> LENGTH: 20
<212> TYPE: DNA
<213> ORGANISM: Artificial Sequence
<220> FEATURE:
<223> OTHER INFORMATION: Synthetic

<400> SEQUENCE: 7
actgaattca cccccactga                                               20

<210> SEQ ID NO 8
<211> LENGTH: 21
<212> TYPE: DNA
<213> ORGANISM: Artificial Sequence
<220> FEATURE:
<223> OTHER INFORMATION: Synthetic

<400> SEQUENCE: 8
aagcaagcaa gcagaatttg g                                             21

<210> SEQ ID NO 9
<211> LENGTH: 21
<212> TYPE: DNA
<213> ORGANISM: Artificial Sequence
<220> FEATURE:
<223> OTHER INFORMATION: Synthetic

<400> SEQUENCE: 9
aagagaccat gcaggctacc a                                             21

<210> SEQ ID NO 10
<211> LENGTH: 20
<212> TYPE: DNA
<213> ORGANISM: Artificial Sequence
<220> FEATURE:
<223> OTHER INFORMATION: Synthetic
```

```
<400> SEQUENCE: 10
acaagttggc caggctgatg                                              20
```